(12) United States Patent
Schraga

(10) Patent No.: US 8,986,249 B2
(45) Date of Patent: Mar. 24, 2015

(54) RETRACTABLE NEEDLE ASSEMBLY AND SYRINGE UTILIZING THE SAME

(75) Inventor: Steven Schraga, Surfside, FL (US)

(73) Assignee: Stat Medical Devices, Inc., North Miami Beach, FL (US)

( * ) Notice: Subject to any disclaimer, the term of this patent is extended or adjusted under 35 U.S.C. 154(b) by 152 days.

(21) Appl. No.: 12/752,186

(22) Filed: Apr. 1, 2010

(65) Prior Publication Data

US 2010/0262119 A1    Oct. 14, 2010

Related U.S. Application Data

(60) Provisional application No. 61/167,741, filed on Apr. 8, 2009.

(51) Int. Cl.
*A61M 5/00* (2006.01)
*A61M 5/32* (2006.01)
*A61M 5/315* (2006.01)
*A61M 5/50* (2006.01)

(52) U.S. Cl.
CPC ......... *A61M 5/3234* (2013.01); *A61M 5/31515* (2013.01); *A61M 5/3202* (2013.01); *A61M 5/502* (2013.01); *A61M 5/508* (2013.01); *A61M 2005/3231* (2013.01); *A61M 2005/3235* (2013.01); *A61M 2005/3236* (2013.01); *A61M 2005/3239* (2013.01)
USPC .......................................... 604/110; 604/220

(58) Field of Classification Search
CPC ... A61M 5/3234; A61M 5/508; A61M 5/322; A61M 2005/3241
USPC ........................ 604/110, 194–196, 220, 225
See application file for complete search history.

(56) References Cited

U.S. PATENT DOCUMENTS

| | | | |
|---|---|---|---|
| 4,650,468 A | | 3/1987 | Jennings, Jr. |
| 4,929,238 A | | 5/1990 | Baum |
| 4,946,441 A | * | 8/1990 | Laderoute ............... 604/110 |
| 5,002,533 A | | 3/1991 | Jullien |
| 5,019,044 A | * | 5/1991 | Tsao .................... 604/110 |
| 5,049,133 A | * | 9/1991 | Villen Pascual ........... 604/110 |
| 5,053,010 A | | 10/1991 | McGary et al. |
| 5,098,402 A | | 3/1992 | Davis |
| 5,125,898 A | | 6/1992 | Kaufhold, Jr. et al. |
| 5,127,906 A | * | 7/1992 | Landry et al. ............ 604/110 |
| 5,167,635 A | | 12/1992 | Haber et al. |
| 5,188,599 A | | 2/1993 | Botich et al. |
| 5,188,600 A | | 2/1993 | Jullien |
| 5,190,526 A | * | 3/1993 | Murray et al. ........... 604/110 |
| 5,211,628 A | * | 5/1993 | Marshall ................. 604/110 |
| 5,242,401 A | | 9/1993 | Colsky |

(Continued)

FOREIGN PATENT DOCUMENTS

| | | |
|---|---|---|
| EP | 2 251 054 | 11/2010 |
| GB | 2 266 667 | 11/1993 |
| WO | WO91/03269 | 3/1991 |

*Primary Examiner* — Emily Schmidt

(74) *Attorney, Agent, or Firm* — Greenblum & Bernstein, P.L.C.

(57) ABSTRACT

An injection device including a barrel, a hollow plunger having a portion structured and arranged to move within the barrel, a needle unit, and a safety system that one of automatically causes the needle unit to retract into the plunger when the plunger reaches a substantially fully depressed position and utilizes a frangible or breakable seal arranged within the plunger. This Abstract is not intended to define the invention disclosed in the specification, nor intended to limit the scope of the invention in any way.

9 Claims, 24 Drawing Sheets

(56) References Cited

U.S. PATENT DOCUMENTS

| | | |
|---|---|---|
| 5,267,977 A | 12/1993 | Feeney, Jr. |
| 5,308,329 A | 5/1994 | Mazur et al. |
| 5,328,475 A | 7/1994 | Chen |
| 5,336,198 A | 8/1994 | Silver et al. |
| 5,344,403 A | 9/1994 | Lee |
| 5,376,080 A | 12/1994 | Petrussa |
| 5,401,249 A | 3/1995 | Shields |
| 5,403,286 A | 4/1995 | Lockwood, Jr. |
| 5,407,436 A * | 4/1995 | Toft et al. .................. 604/195 |
| 5,498,241 A | 3/1996 | Fabozzi |
| 5,531,694 A * | 7/1996 | Clemens et al. ............ 604/110 |
| 5,569,203 A | 10/1996 | Chen |
| 5,591,131 A | 1/1997 | Chen |
| 5,591,138 A | 1/1997 | Vaillancourt |
| 5,814,017 A | 9/1998 | Kashmer et al. |
| 5,858,000 A | 1/1999 | Novacek et al. |
| 6,010,486 A | 1/2000 | Carter et al. |
| 6,074,370 A | 6/2000 | Pressly, Sr. et al. |
| 6,074,373 A | 6/2000 | Sudo et al. |
| 6,083,199 A | 7/2000 | Thorley et al. |
| 6,179,812 B1 * | 1/2001 | Botich et al. ............... 604/110 |
| 6,183,440 B1 | 2/2001 | Bell |
| 6,210,371 B1 | 4/2001 | Shaw |
| D452,000 S | 12/2001 | Crawford et al. |
| 6,368,303 B1 | 4/2002 | Caizza |
| 6,375,640 B1 | 4/2002 | Teraoka |
| 6,461,328 B2 | 10/2002 | Wang et al. |
| 6,517,516 B1 | 2/2003 | Caizza |
| 6,632,198 B2 | 10/2003 | Caizza |
| 6,648,849 B2 | 11/2003 | Tenhuisen et al. |
| 6,840,291 B2 | 1/2005 | Caizza et al. |
| 7,090,656 B1 | 8/2006 | Botich et al. |
| 7,144,387 B2 | 12/2006 | Millerd |
| 7,150,725 B2 | 12/2006 | Wilkinson |
| 7,322,963 B2 | 1/2008 | Goh |
| 7,413,560 B2 | 8/2008 | Chong et al. |
| 7,428,773 B2 | 9/2008 | Newby et al. |
| 7,500,967 B2 | 3/2009 | Thorley et al. |
| 7,604,613 B2 | 10/2009 | Crawford et al. |
| 7,803,132 B2 | 9/2010 | Janek et al. |
| 7,846,135 B2 | 12/2010 | Runfola |
| 7,935,087 B2 | 5/2011 | Judd et al. |
| 8,002,745 B2 | 8/2011 | Kaal et al. |
| 8,012,132 B2 | 9/2011 | Lum et al. |
| 8,021,333 B2 | 9/2011 | Kaal et al. |
| 8,052,654 B2 | 11/2011 | Kaal et al. |
| 8,114,050 B2 | 2/2012 | Kaal et al. |
| 8,147,450 B2 | 4/2012 | Yang |
| 2003/0004491 A1 * | 1/2003 | Tenhuisen et al. ........... 604/502 |
| 2004/0254529 A1 | 12/2004 | Fitzgeald |
| 2005/0159705 A1 | 7/2005 | Crawford et al. |
| 2006/0084913 A1 | 4/2006 | Lo |
| 2008/0154212 A1 | 6/2008 | Schraga |
| 2010/0262119 A1 | 10/2010 | Schraga |
| 2011/0092902 A1 * | 4/2011 | Kiehne ........................ 604/110 |
| 2011/0125130 A1 | 5/2011 | Schraga |
| 2011/0213304 A1 | 9/2011 | Schraga |

* cited by examiner

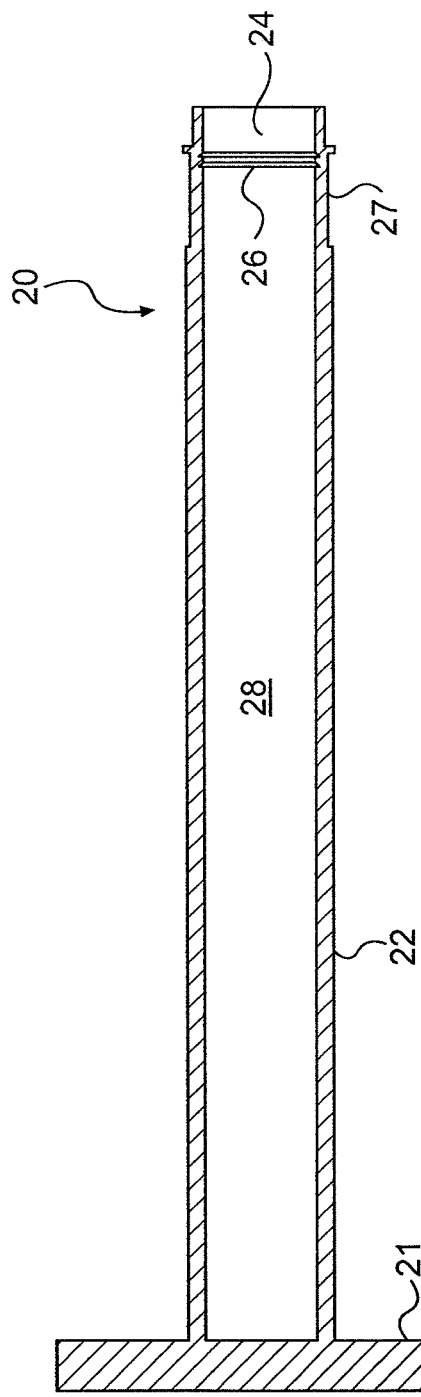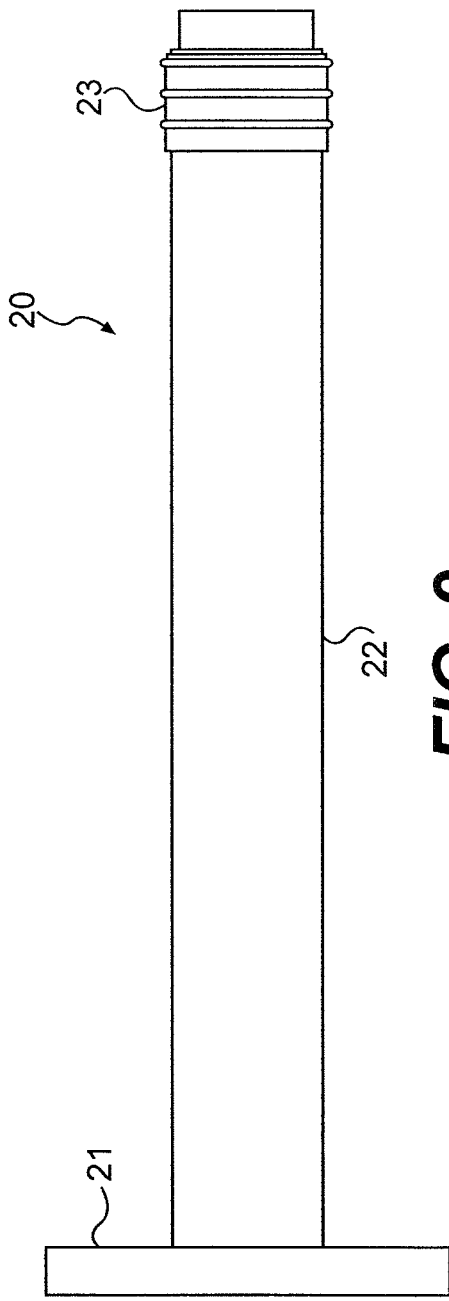

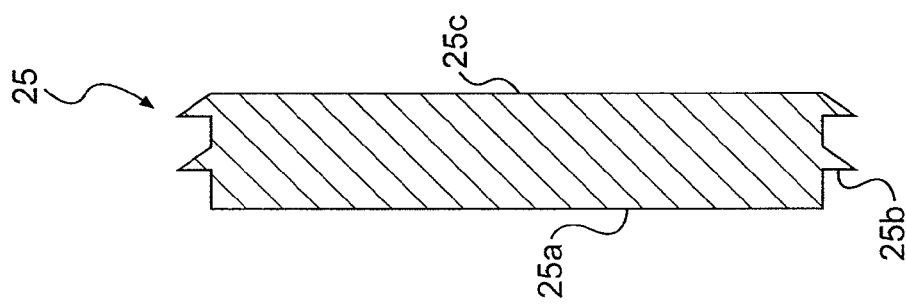
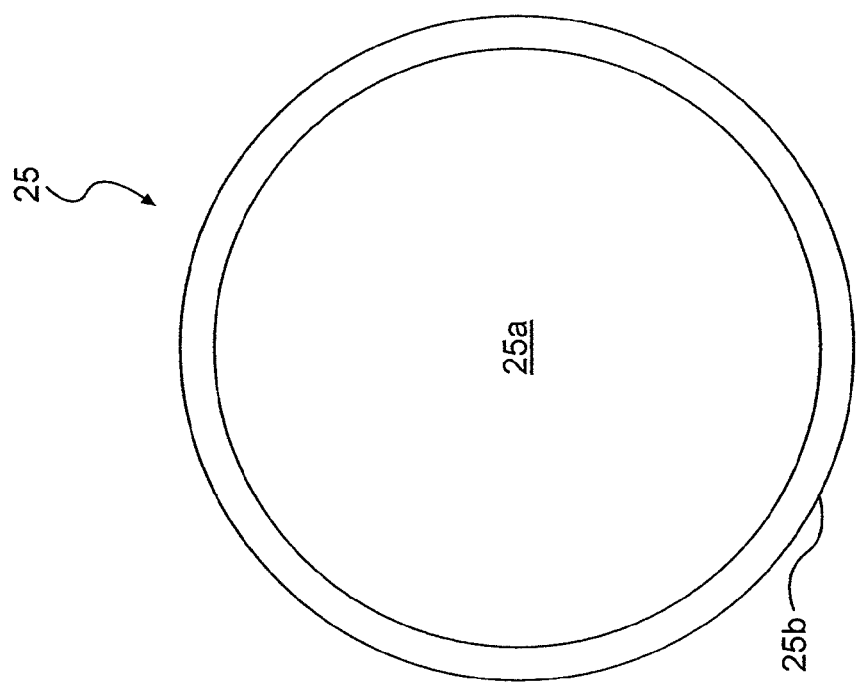
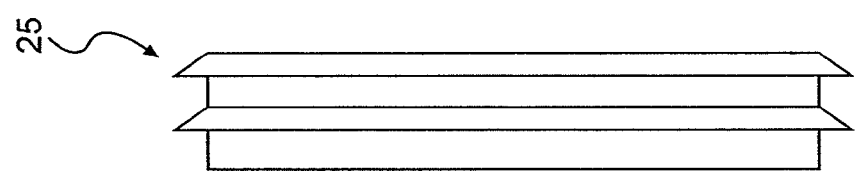

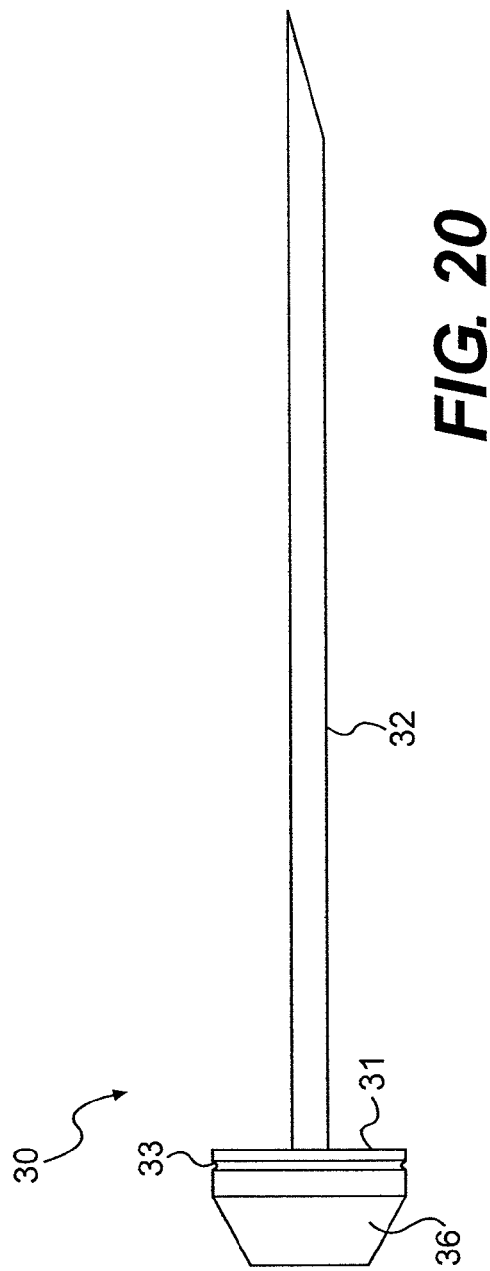
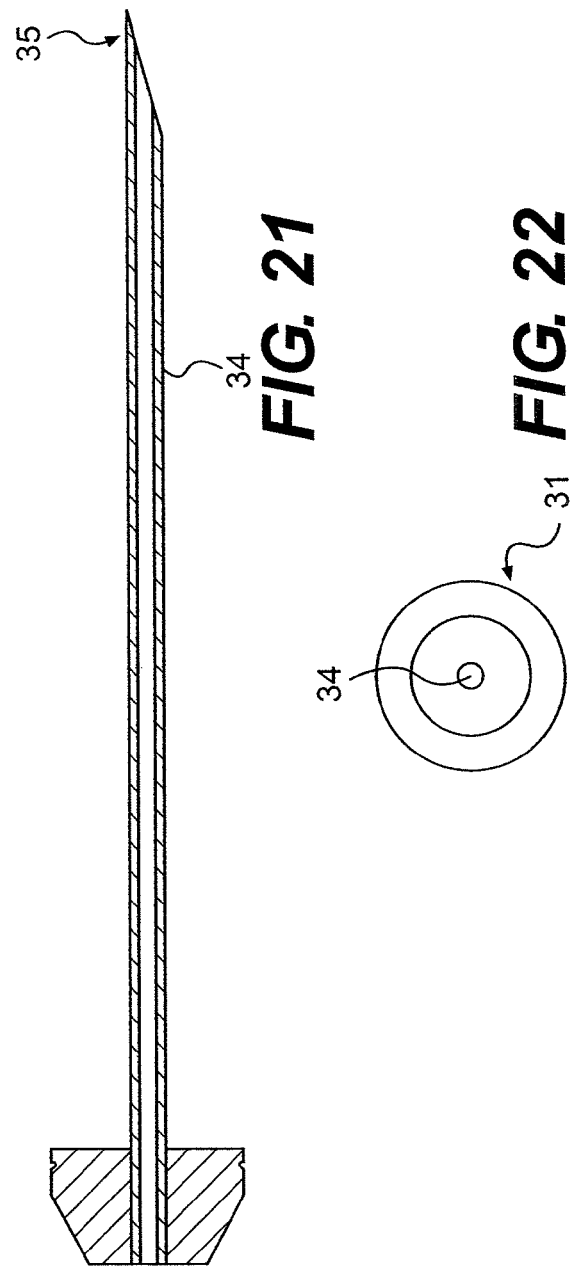
FIG. 20
FIG. 21
FIG. 22

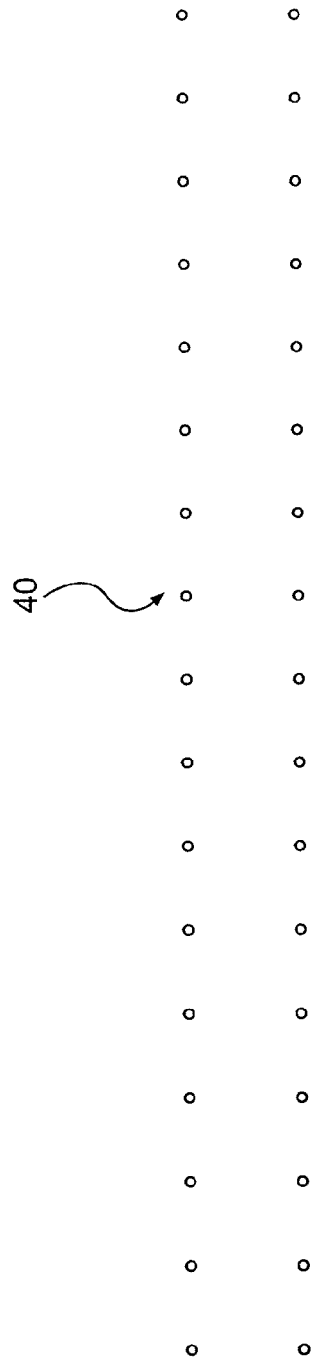

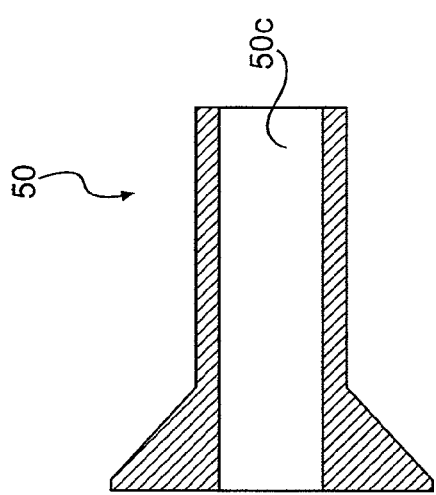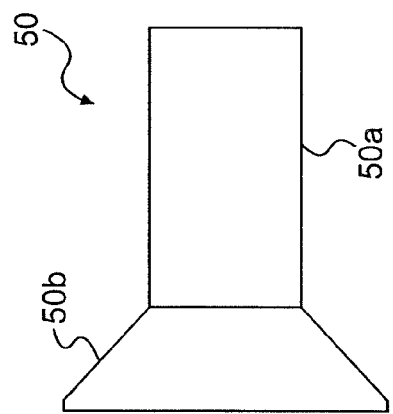

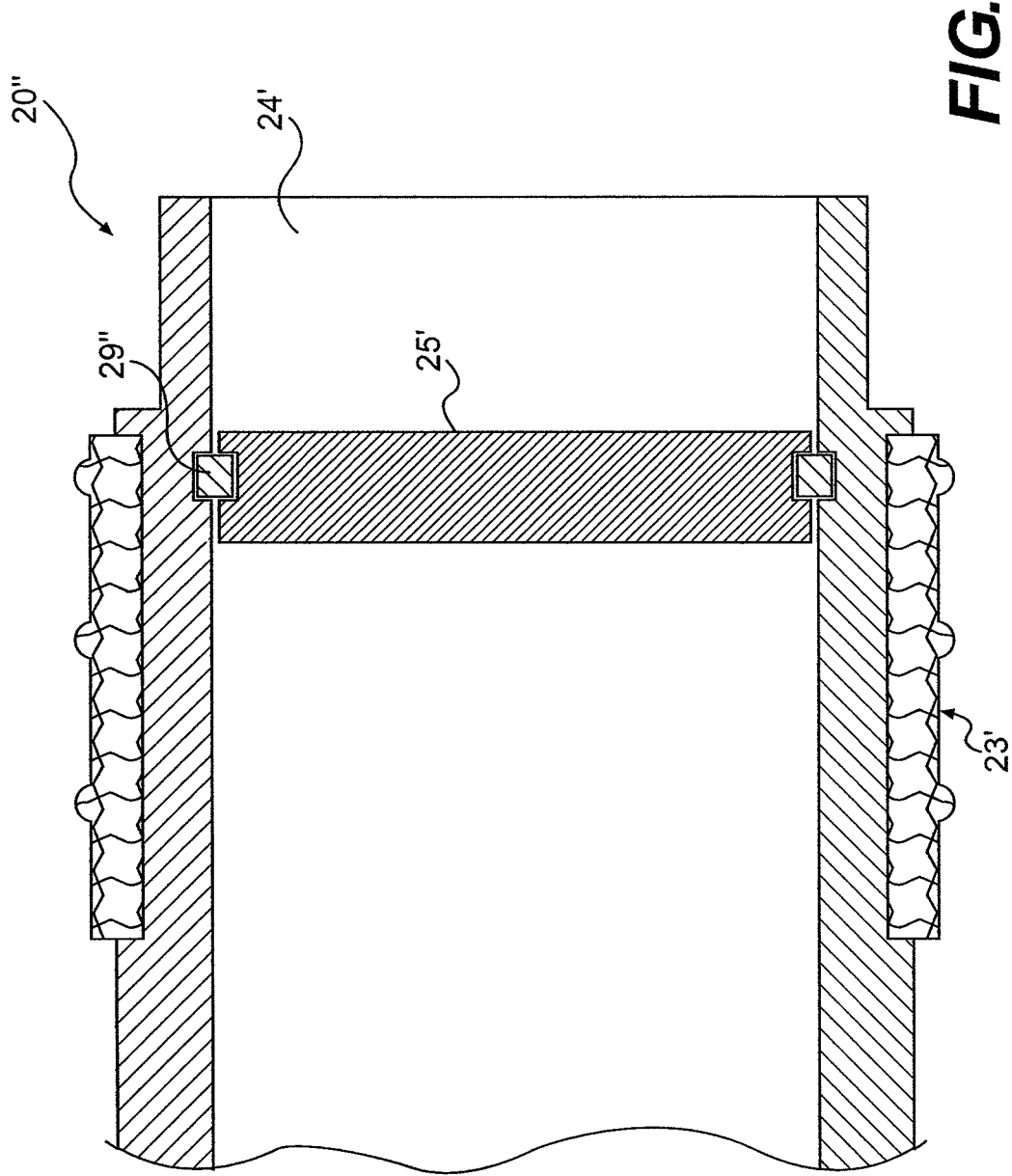

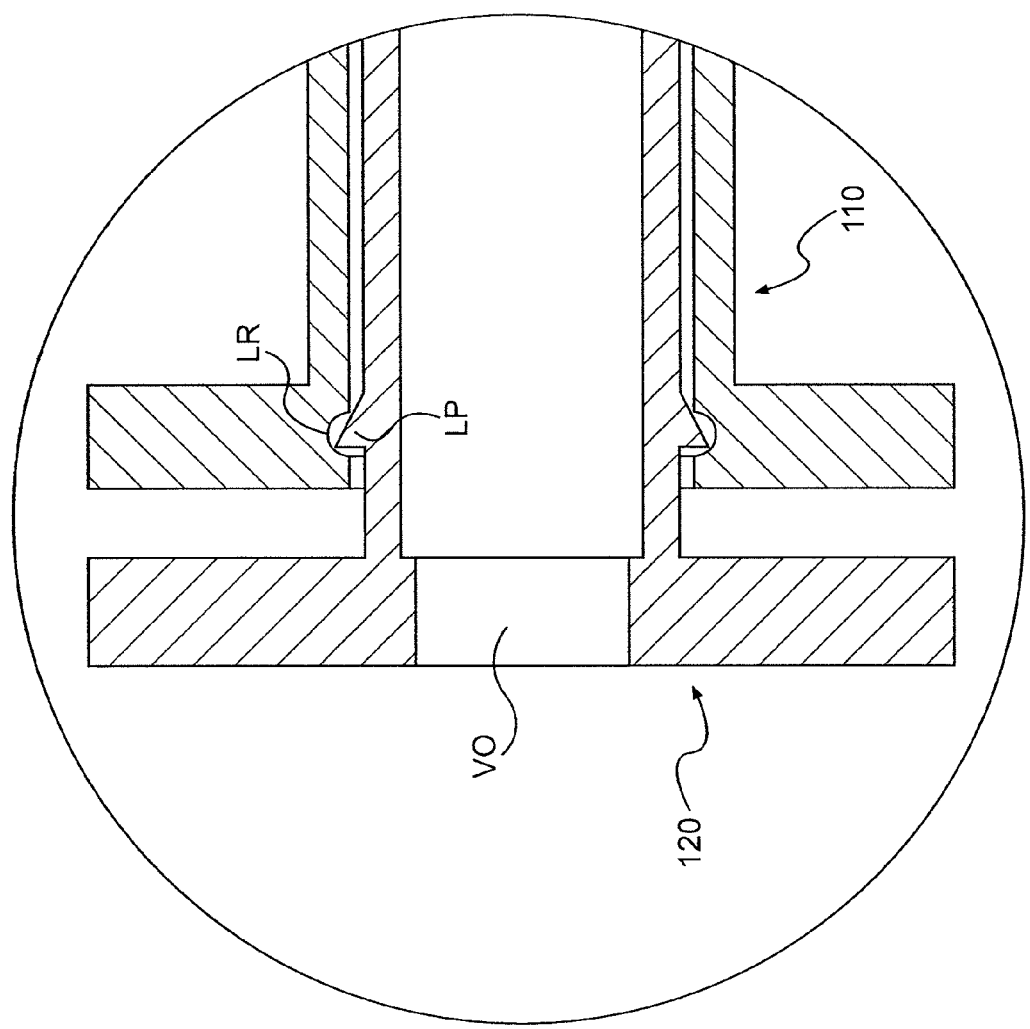

RETRACTABLE NEEDLE ASSEMBLY AND SYRINGE UTILIZING THE SAME

CROSS-REFERENCE TO RELATED APPLICATIONS

The instant application is a US non-provisional application based on U.S. provisional application No. 61/167,741, filed Apr. 8, 2009, the disclosure of which is hereby expressly incorporated by reference hereto in its entirety.

BACKGROUND OF THE INVENTION

1. Field of the Invention

This invention relates generally to syringes, e.g., hypodermic syringes, such are utilized for injection of medicament into the body tissues of human and animal patients. More specifically, this invention relates to a hypodermic syringe having a plunger, piston and needle support structure or needle unit that permits retraction of the needle support and its needle into the plunger of the syringe to prevent the possibility of inadvertent needle pricks and which incorporates a frangible plunger seal that may be broken away to prevent subsequent use or re-use of the syringe.

This invention also relates to single-use syringes which automatically retracts the needle into the syringe when the plunger is substantially fully depressed which is more easily and/or less costly to produce.

This invention also relates to syringes which can be used only once, i.e., single-use syringes, and/or to syringes which utilize a built-in safety system which cannot be easily overridden by a user thereof.

2. Discussion of Background Information

In hospitals, nursing home facilities and the like, injection of medicament into the body tissues of patients is done on a daily basis. Typical hypodermic syringes are provided with a barrel having a needle that is fixed or removably attached at one end thereof. A plunger typically having an elastomeric piston is movable within the barrel to load the barrel with liquid medicament by suction as the plunger and piston are moved within the barrel in a direction away from the needle. After the needle has penetrated the body tissues of the patient, as the direction of movement of the plunger and piston are reversed and the piston is forced toward the needle, medicament contained within the barrel will be injected through the needle into the body tissues.

After hypodermic syringes have been used in this manner, those syringes that are disposable present a significant problem to users, e.g., hospital or nursing home staff, because the possibility of inadvertent needle pricks subject personnel to the possibility of cross-contamination by, among other things, virile or bacterial contaminants that might be present on the needle after its use. In an effort to avoid the possibility of inadvertent needle pricks special waste containers are often provided at hospital facilities into which the used disposable hypodermic syringes are placed. These containers and the syringes contained therein are then disposed of in a specifically organized manner to insure against the possibility of inadvertent infectious contamination of nursing personnel. Further, refuse handlers and other persons who might inadvertently come into contact with the used hypodermic syringes are also subject to the same hazards. Often times the needles themselves are bent over so as to minimize the possibility of inadvertent needle pricks and to preclude the possibility of subsequent use of disposable hypodermic syringes.

In certain situations, medicaments are injected into patients and not quickly thereafter discarded properly. Instead, the used syringe is placed in a temporary position. After the procedure has ended, the syringe can be manually recovered for disposal. However, between the time of use and the time of disposal, there is the possibility that inadvertent needle pricks will occur. Accordingly, it is desirable to provide a suitable way protecting personnel, e.g., nursing personnel, paramedics and other persons, from the hazards of inadvertent needle pricks as they go about their daily tasks.

It is therefore desirable to provide a syringe that includes a system for rendering the needle thereof to a protected, completely encapsulated condition such that it is less likely to cause, after use, an inadvertent needle prick during its handling or during its disposal. It is also desirable to provide a syringe having the capability of causing the automatic retraction of the needle to a position inside the plunger of the syringe and maintaining the needle in its retracted position so that the needle of the syringe is always enclosed after its use, thus precluding the possibility that the needle might cause an accidental needle prick as the syringe is subsequently handled. It is also desirable to provide a syringe of the disposable type that is provided with facility for rendering it completely inoperative such that it can not be subsequently used. Additionally, it is desirable to provide for a syringe which also has minimal dead-space so that it can be ideally used for injecting very expensive medicaments with minimal waste. Finally, it is desirable to provide for a syringe which also has a system for selectively locking the plunger in a substantially fully depressed position so that the syringe can have dual, multiple, and/or parallel safety systems, i.e., one system can include causing the needle unit to retract into the plunger and another system can include locking the plunger in a substantially fully depressed position.

SUMMARY OF THE INVENTION

According to one non-limiting aspect of the invention there is provided an injection device comprising a barrel, a hollow plunger having a portion structured and arranged to move within the barrel, a needle unit, and a safety system that one of automatically causes the needle unit to retract into the plunger when the plunger reaches a substantially fully depressed position and utilizes a frangible or breakable seal arranged within the plunger.

The injection device may be a single-use syringe. The barrel may comprise a cylindrically shaped internal space structured and arranged to receive therein a medicine. The barrel may further comprise a proximal opening within which the needle unit is at least one of press fit and in sealing engagement therewith. The plunger may comprise a piston arranged at a proximal area of the plunger and an actuating end arranged in front of the piston. The plunger may further comprise at least one of the piston being an elastomer or rubber piston, a hollow space sized and configured to receive therein the needle unit in its entirety, and a locking member adapted to lock with a locking member arranged on the barrel. The barrel, the plunger, and a hub portion of the needle unit may each comprise a synthetic resin material. The needle unit may comprise a generally cylindrical hub and a hollow needle projecting from the hub. The needle may comprise at least one of metal and stainless steel. The barrel may comprise at least one releasable retaining member which releasably retains the needle unit in an initial position. The barrel may comprise plural releasable retaining members which each releasably retain the needle unit in an initial position. The barrel may comprise at least one deflectable retaining member which releasably retains the needle unit in an initial position. The barrel may comprise plural deflectable retaining members which each releasably retain the needle unit in an initial position.

The device may further comprise a locking arrangement that is structured and arranged to lock a distal end portion of the plunger to the barrel. The device may further comprise a locking arrangement selectively locking a portion of the plunger to the barrel upon the plunger reaching a substantially fully depressed position. The device may further comprise a biasing member, wherein, when the plunger is moved to a full injection position, the needle unit is automatically caused to retract into the plunger via the spring. The device may further comprise a spring arranged within the barrel, wherein, when the plunger is moved to a full injection position, the needle unit is automatically caused to retract into the plunger via the spring. The device may further comprise a system providing an indication to the user that further forward movement of the plunger will cause the needle unit to automatically retract into the plunger. The device may further comprise a system providing an indication to the user that at least one of the plunger has reached a full injection position and the further forward movement of the plunger will cause the needle unit to automatically retract into the plunger.

According to one non-limiting aspect of the invention there is provided a syringe comprising a barrel, a plunger having a portion structured and arranged to move within the barrel, a needle unit, and a safety system that one of automatically causes the needle unit to retract into the plunger when the plunger reaches a substantially fully depressed position and utilizes a frangible or breakable seal arranged within the plunger.

The syringe may further comprise a system providing an indication to the user that the plunger has reached a full injection position and the further forward movement of the plunger will cause the needle unit to automatically retract into the plunger.

According to one non-limiting aspect of the invention there is provided a single-use syringe comprising a barrel, a hollow plunger having a portion structured and arranged to move within the barrel, a needle unit, and a safety system that one of automatically causes the needle unit to retract into the plunger when the plunger reaches a substantially fully depressed position and utilizes a frangible or breakable seal arranged within the plunger.

The syringe may further comprise a system providing an indication to the user that the plunger has reached a full injection position and the further forward movement of the plunger will cause the needle unit to automatically retract into the plunger.

According to one non-limiting aspect of the invention there is provided a method of using the injection device described above, wherein the method comprises moving the plunger away from the needle unit so as to cause a desired amount of medicine to enter into the barrel and moving the plunger towards the needle unit so as to cause medicine to exit the barrel through the needle. The method may further comprise locking the plunger to the barrel to prevent re-use of the syringe.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 1 shows the device with a safety cap installed thereon. The device is in an initial prior-use and/or packaged configuration;

FIG. 8 shows a side cross-section view of the plunger used on the first non-limiting embodiment shown in FIG. 1 and with the plunger piston and inner seal removed;

FIG. 9 shows a side view of the plunger of FIG. 8 with the plunger piston installed thereon;

FIG. 12 shows a side view of the inner seal used on the plunger shown in FIG. 1;

FIG. 13 shows a front end view of the inner seal shown in FIG. 12;

FIG. 14 shows a side cross-section view of the inner seal shown in FIG. 12;

FIG. 20 shows a side view of the needle unit used in the device shown in FIG. 1;

FIG. 21 shows a side cross-section view of the needle unit shown in FIG. 20;

FIG. 22 shows a rear end view of the needle unit shown in FIG. 20;

FIG. 23 shows a side cross-section view of the spring used in the device shown in FIG. 1;

FIG. 24 shows a rear end view of the spring shown in FIG. 23;

FIG. 25 shows a side cross-section view of the needle sealing guide member used in the device shown in FIG. 1;

FIG. 26 shows a side view of the needle sealing guide member shown in FIG. 25;

FIG. 27 shows an enlarged partial view of another embodiment of a plunger which can be used on a device of the type shown in FIG. 1. The plunger is similar to that used in FIG. 1 except that the inner seal is axially retained within the plunger via a separately formed ring;

FIG. 33 shows an enlarged partial view of another modified version of the device of FIG. 1. In this embodiment, the device of FIG. 1 is modified to include a locking system to prevent re-use of the device as well as an optional vent opening. The locking system locks the plunger to the syringe body when the plunger is fully or nearly fully depressed;

In FIG. 35, the inner seal is axially retained within the plunger. In FIG. 34, the inner seal has been moved back sufficiently to cause the inner seal to break the frangible projection of the plunger;

In FIG. 36, the frangible projection of the plunger has annular v-shaped recesses which weaken the projection so that it breaks (via shearing forces) in a predictable manner.

DETAILED DESCRIPTION OF THE INVENTION

Figure 1:
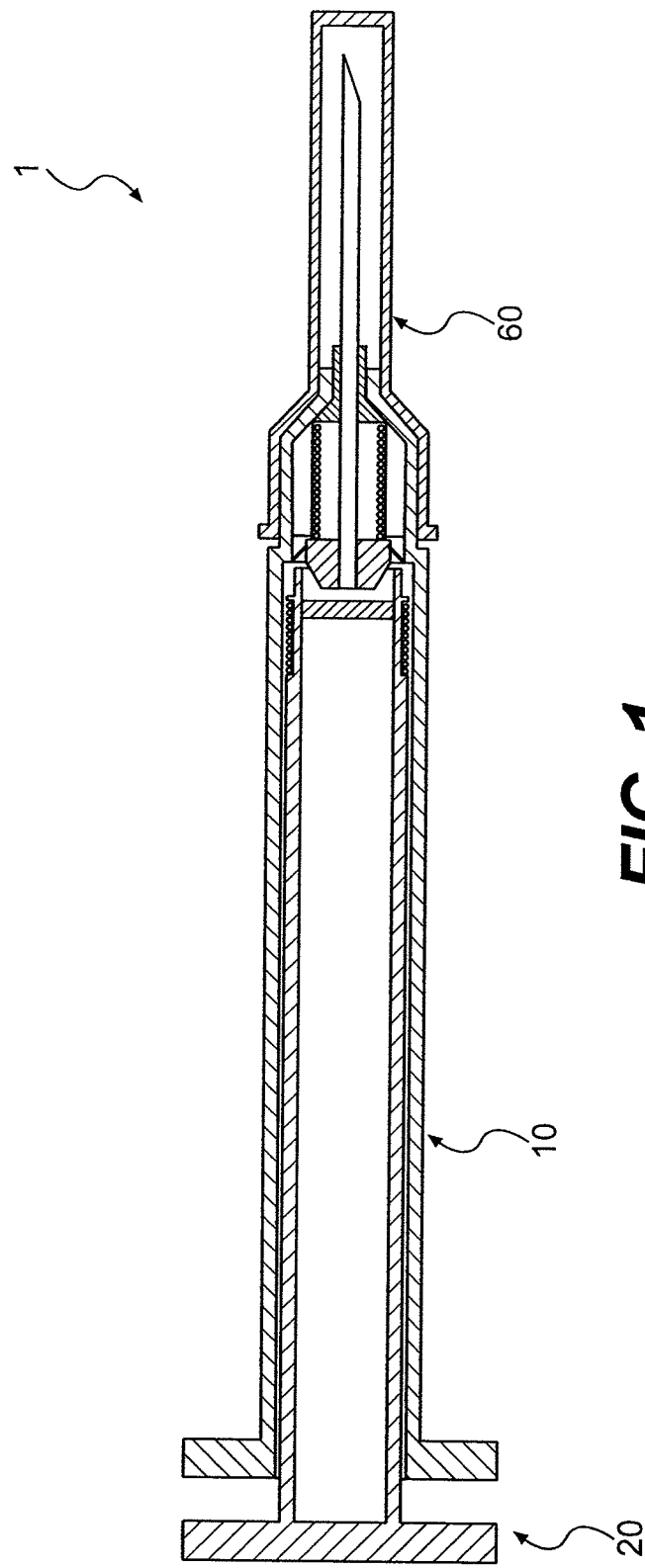
FIG. 1 shows a side cross-section view of a first non-limiting embodiment of the device according to the invention. The needle is not shown in cross-section.

Referring now to the drawings and first to FIGS. 1-17 and 20-26 which shows a first embodiment of an injection device 1. In embodiments, the device is a retractable hypodermic syringe. The syringe includes a generally elongate cylindrical barrel 10 having a transverse flange 11 arranged at a distal end of the barrel 10. The barrel 10 includes a main generally cylindrical section 12. A proximal end of the barrel 10 includes a reduced diameter section 13. A safety cap 60 is removably disposed on a proximal end of the syringe body 10.

Figure 2:
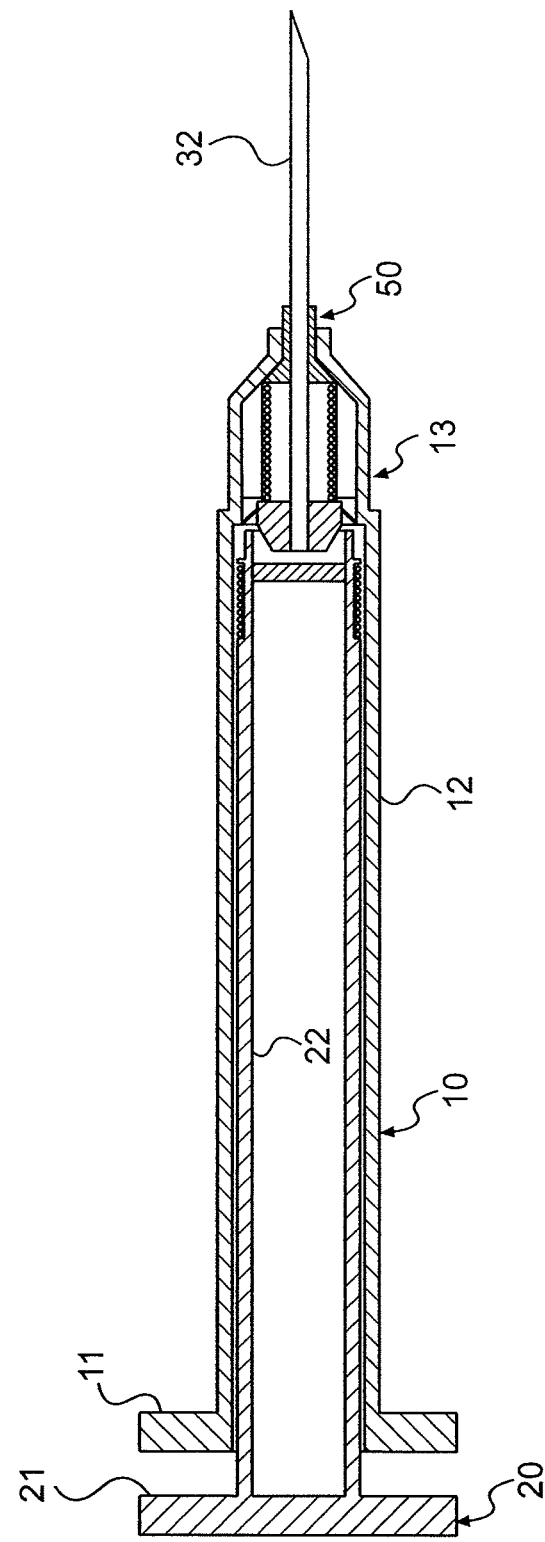
FIG. 2 shows the device of FIG. 1 after the safety cap is removed and in a ready-to-use position.

A needle support 30 has a hub portion 31 that is substantially axially retained within a proximal area of the body 10 (see FIG. 3) and includes a rear end surface which can contact an inner seal 25 of a plunger 20 as will be described in detail below. The needle support 30 also has a main needle portion 32 that has a rear end fixed within a needle hub 31 and a proximal end that is pointed or a puncturing end which extends out past the proximal end of the syringe body 10. A sealing guide member 50 provides sealing between the needle 32 and the syringe body 10, also allows the needle 32 to slide into the syringe 1 as will be described below. A spring 40 is arranged within the section 13 and the syringe body 10, and in the configuration shown in FIG. 2, is fully or nearly fully compresses. The spring 40 biases the needle unit 30 towards a distal end of the syringe 1.

Substantially arranged within the barrel 10 of the syringe is movably disposed a plunger 20. The plunger 20, like the syringe body 10, includes an end flange 21 which is typically engaged by the thumb of the user while the transverse flange 11 is engaged by the fingers of the user in order to enable the plunger 20 to be forced into the barrel 10 for the purpose of expelling the medicament from the barrel 10 through the needle 32. The plunger 20 additionally includes a generally cylindrical space 22 which is sized to receive therein the needle unit 30 (see FIG. 5). A piston 23 (see FIG. 9) is arranged on a proximal end of the plunger 10. The plunger 20 also utilizes a proximal engaging end 24 which is sized and configured to engage with deflectable retaining members 15 (see FIGS. 6 and 7) when the plunger 20 is fully depressed. An inner seal or sealing member 25 is arranged within the plunger 20. As is apparent from FIGS. 6 and 7, the seal 25 has frangible circumferential projections which are sized and configured to break and/or shear off when the plunger 20 is depressed to the point where the seal 25 contacts the hub 31. Before the projections of the seal 25 break, they provide sealing between the seal 25 and the plunger 20. This sealing ensures that no medication passes into the plunger space 22 until the seal 25 is broken.

Figure 6:
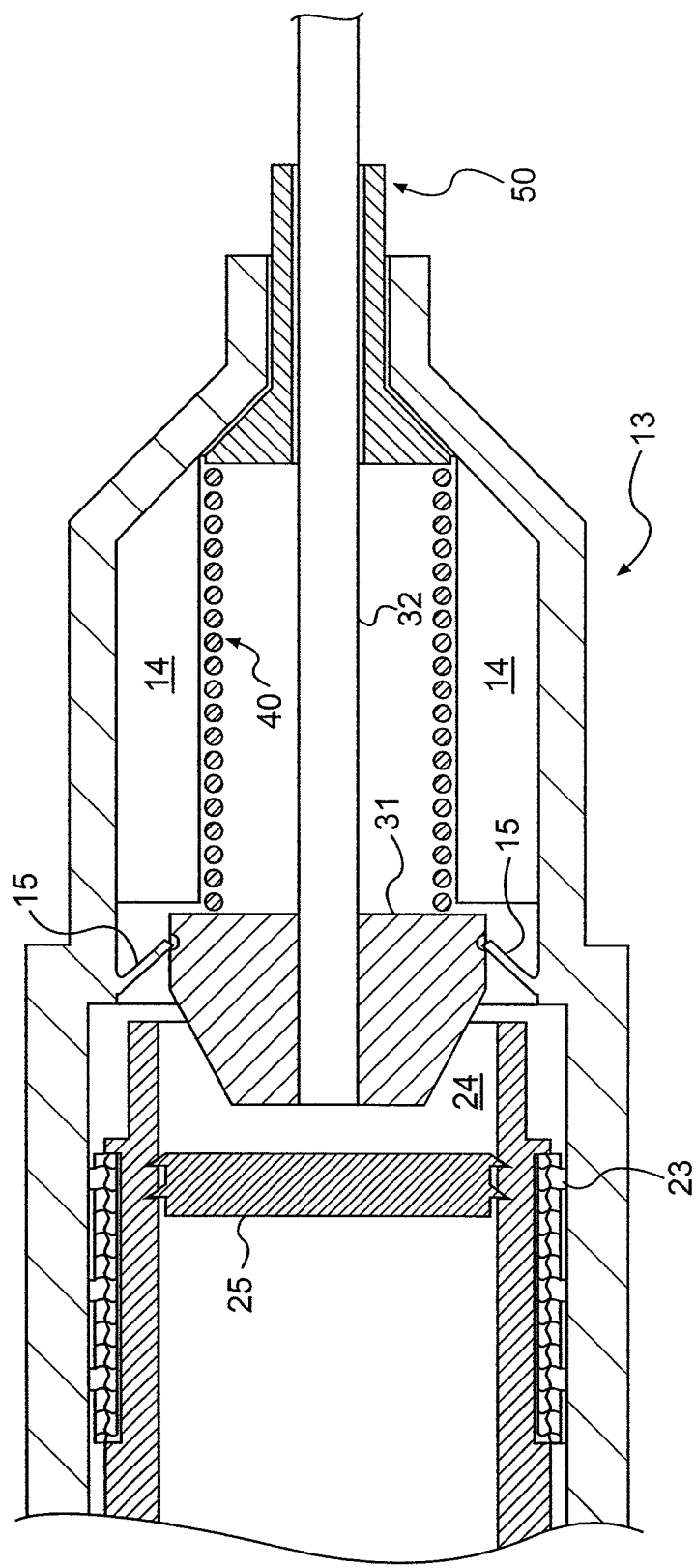
FIG. 6 shows an enlarged partial view of the device of FIG. 4 just before the plunger reaches the fully depressed position.
Figure 7:
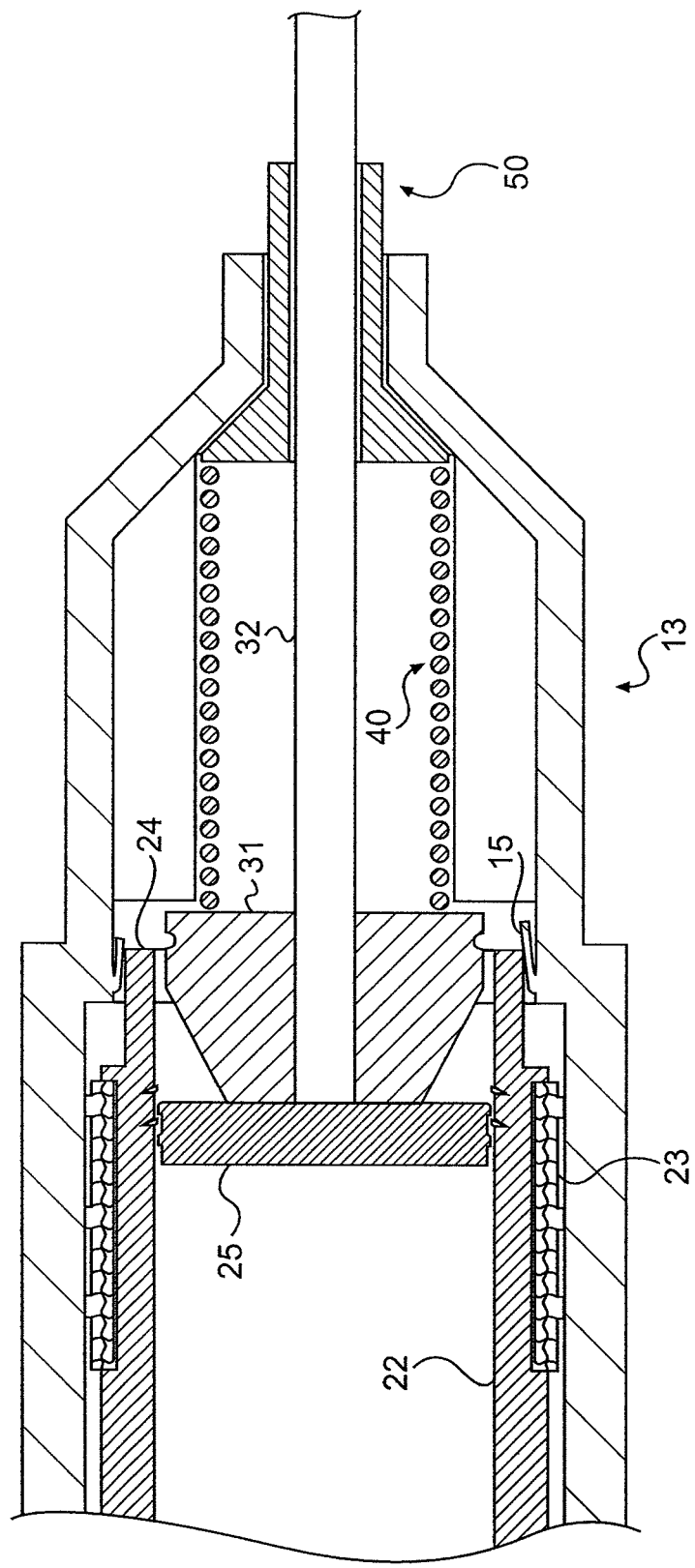
FIG. 7 shows an enlarged partial view of the device of FIG. 4 just as the plunger reaches the fully depressed position thereby causing deflection of the retaining members and breaking of the frangible plunger seal caused by movement of the plunger against a rear end of the needle hub.
Figure 11:
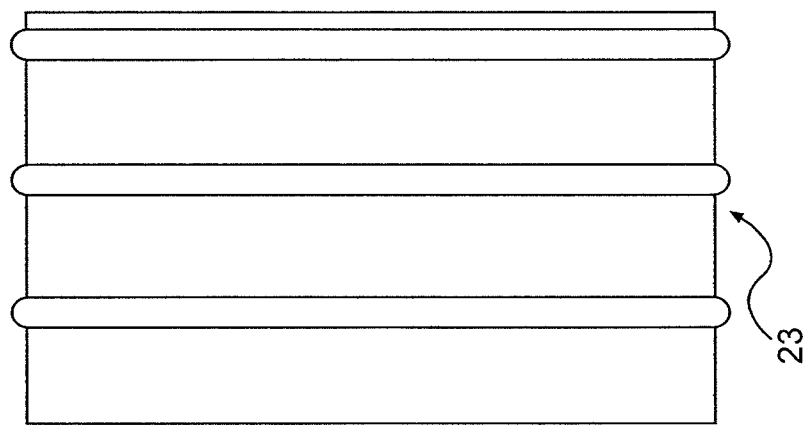
FIG. 11 shows a side view of the plunger piston shown in FIG. 10.
Figure 10:
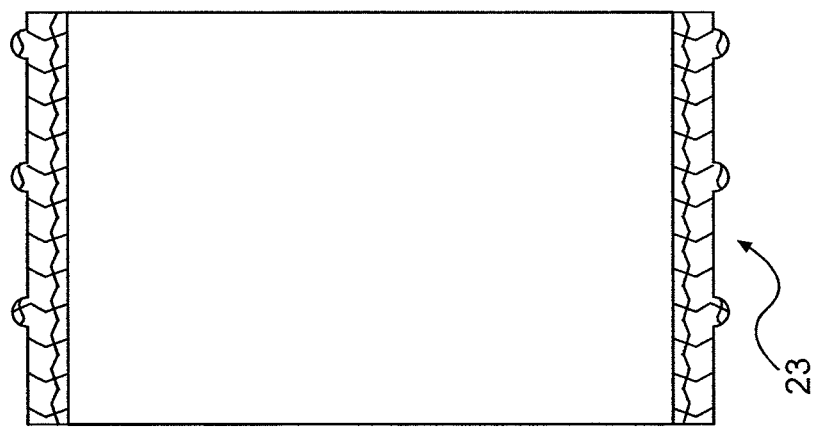
FIG. 10 shows a side cross-section view of the plunger piston used on the plunger shown in FIG. 9.

As is apparent from FIGS. 6 and 7, to unsure that the needle unit 30 is prevented from moving forwards when the plunger 20 is fully depressed, a plurality of stop projections or ribs 14 are arranged within the section 13 of the syringe body 10.

Figure 3:
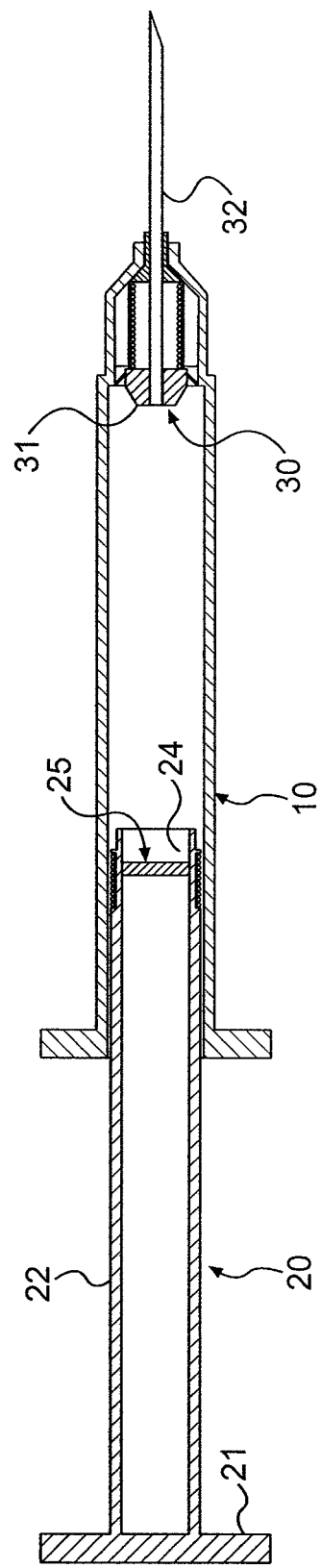
FIG. 3 shows the device of FIG. 2 with the plunger retracted as would occur when medicine is caused to be suctioned into the syringe via the needle.
Figure 4:
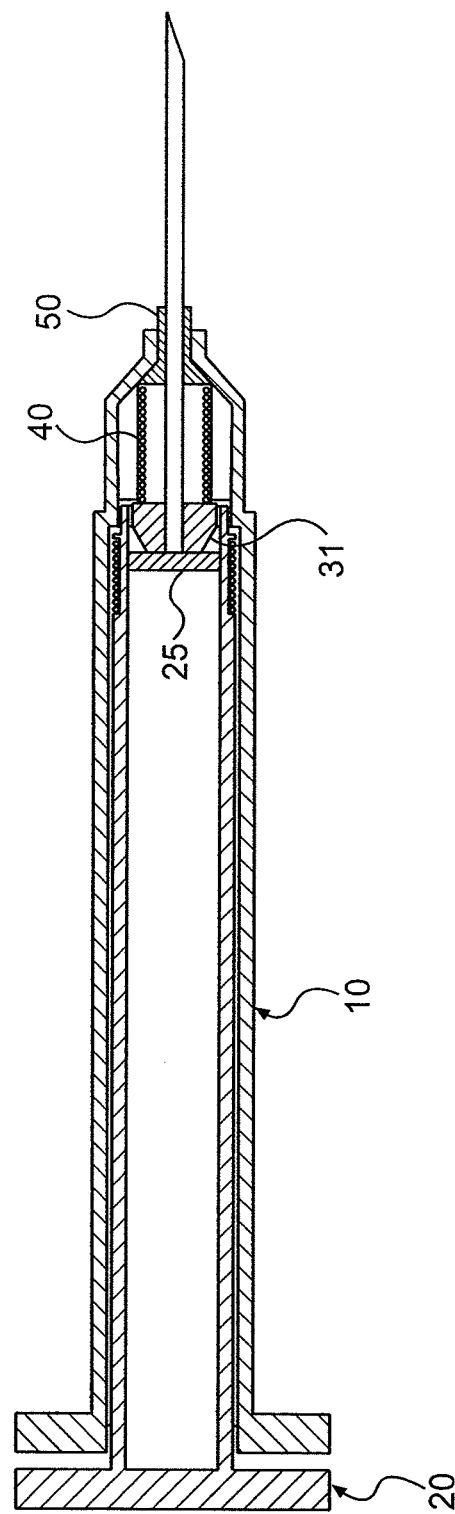
FIG. 4 shows the device with the plunger fully depressed as would occur during injection. In this position, the leading end of the plunger has moved deflectable retaining members out of locking engagement with the needle hub. Moreover, a rear end of the needle hub has caused an inner seal, i.e., a frangible plunger seal, to come out of sealing engagement with the needle hub.
Figure 5A:
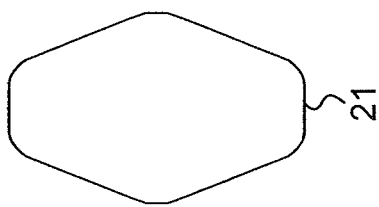
FIG. 5a shows a rear end view of the device of FIG. 5.
Figure 5:
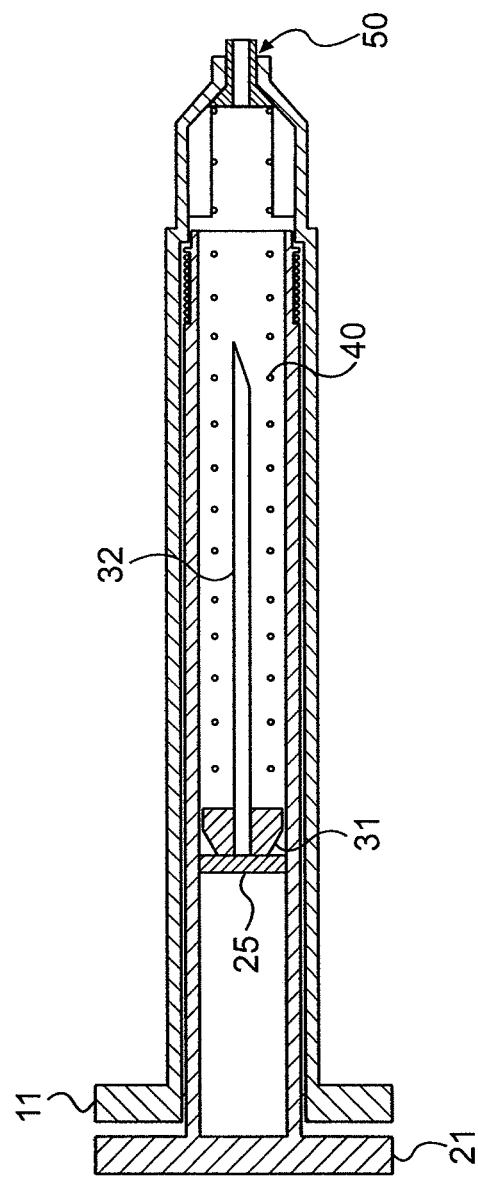
FIG. 5 shows the device after the needle unit is caused to automatically retract into the plunger under the biasing force of a spring. The configuration shown in FIG. 5 occurs automatically when the plunger reaches the position shown in FIG. 4.

The operation of the device shown FIGS. 1-7 will now be described. Once the user obtains the device 1 shown in FIG. 1, he or she can then remove the safety cap 60. The device 1 so shown in FIG. 2 can now be used for, e.g., injection. This can occur when the user injects the needle 32 into a medication container and withdraws the plunger 20 as shown in FIG. 3. This causes medication fluid to fill the space in the body 10 between the plunger piston 23 and seal 25 and the sealing member 50. As this point, the user can move the plunger 20 forwards slightly to remove any air in the syringe 1. The needle 32 can then be injected into, e.g., tissue. Then, the user will depress the plunger 20 to cause the medication to pass out of the needle 32. Once fully or nearly fully depressed, the proximal end 24 of the plunger 20 contacts the deflectable retaining members 15 (see FIGS. 6 and 7) and causes them to deflect out of locking and/or retaining engagement with the hub 31. Since engagement between the deflectable retaining members 15 and the hub 31 is the only mechanism which presents the spring 40 from moving the needle unit 30 backwards, once this engagement is removed, the needle unit 30 will be forced backwards by the spring 40. Also, once fully or nearly fully depressed, the seal 25 of the plunger 20 contacts the rear surface of the hub 31 (see FIGS. 6 and 7). Since the ribs 14 prevent any forward movement of the hub 31, contact between the seal 25 and the hub 31 causes the frangible sealing projections of the seal 25 to shear or break. At this point, the spring 40 automatically expands axially and pushes the needle unit 30 and seal 25 into the space 28 disposed inside the plunger 20 as shown in FIG. 5. This action withdraws the needle 32 into the syringe and renders the device 1 unusable. The device 1 of FIG. 5 can then be safely disposed of without the user having to worry about being accidently pricked by the needle 32, which is safely disposed inside the plunger 20.

In embodiments, the engagement between the deflectable retaining members 15 and the hub 31 is removed or disengages prior to the sealing engagement between the seal 25 and the plunger 20. In other embodiments, the engagement between the deflectable retaining members 15 and the hub 31 is removed or disengages just prior to the sealing engagement between the seal 25 and the plunger 20. In embodiments, the engagement between the deflectable retaining members 15 and the hub 31 is not removed or disengaged until after the frangible sealing engagement between the seal 25 and the plunger 20 is broken. In embodiments, the engagement between the deflectable retaining members 15 and the hub 31 is not removed or disengaged until just after the frangible sealing engagement between the seal 25 and the plunger 20 is broken. In embodiments, the force required to unlock or remove the engagement between the deflectable retaining members 15 and the hub 31 is less than that required to break the sealing engagement between the seal 25 and the plunger 20. In embodiments, the force required to unlock or remove the engagement between the deflectable retaining members 15 and the hub 31 is greater than that required to break the sealing engagement between the seal 25 and the plunger 20. In embodiments, the force required to unlock or remove the engagement between the deflectable retaining members 15 and the hub 31 is substantially equal to that required to break the sealing engagement between the seal 25 and the plunger 20. In embodiments, a noise is produced (providing an auditory signal to the user) when the engagement between the deflectable retaining members 15 and the hub 31 is removed. In embodiments, a noise is produced (providing an auditory signal to the user) when the sealing engagement between the seal 25 and the plunger 20 is broken. In embodiments, a visual indication is produced (providing a visual signal to the user) when the engagement between the deflectable retaining members 15 and the hub 31 is removed. In embodiments, a visual indication is produced (providing a visual signal to the user) when the sealing engagement between the seal 25 and the plunger 20 is broken. Such visual indicators can be facilitated by making the plunger 20 and body 10 substantially transparent and/or translucent.

FIGS. 8 and 9 show views of the plunger 20 used on the first non-limiting embodiment shown in FIG. 1. The plunger 20, in embodiments, is a one-piece integrally formed member to which is axially secured a piston 23 and an inner seal 25. The plunger 20 includes a distal flange 21, a main cylindrical section 22, a generally cylindrical proximal end 24, one or more inner generally circumferential tapered recesses 26, a generally cylindrical recess 27 sized and configured to receive therein and axially retain the piston 23, and a generally cylindrical space 28.

FIGS. 8 and 9 show views of the piston 23 used on the plunger of FIGS. 8 and 9. The piston 23, in embodiments, is a one-piece integrally formed member to which is axially secured within the recess 27 of the plunger 20. In embodiments, it can be substantially similar at pistons conventionally used in syringes which include plural external circumferential sealing projections.

FIGS. 12-14 show views of the inner seal 25 used on the plunger of FIGS. 8 and 9. The seal 25, in embodiments, is a one-piece integrally formed member to which is axially secured to an inner portion of the plunger 20. In embodiments, the seal 25 includes a distal or rear surface 25a, one or more tapered external circumferential projections 25b, and a proximal surface 25c. The one or more tapered external circumferential projections 25b each extend into one of the recesses 26 of the plunger 20. The tapered external circumferential projections 25b are designed to be frangible and sized and configured to shear upon experiencing a predetermined force applied to the surface 25c. The shape, i.e., rearward orientation, of the tapered external circumferential projections 25b is such that a force applied to the surface 25c will cause the projections 25b to grip recesses 26 by a greater amount and such that a force applied to the surface 25a will cause the projections 25b to grip recesses 26 by a lesser amount. In embodiments, a force applied to the surface 25a will cause the projections 25b to start to move out of engagement with the recesses 26 by a significant amount without breaking.

Figure 15:
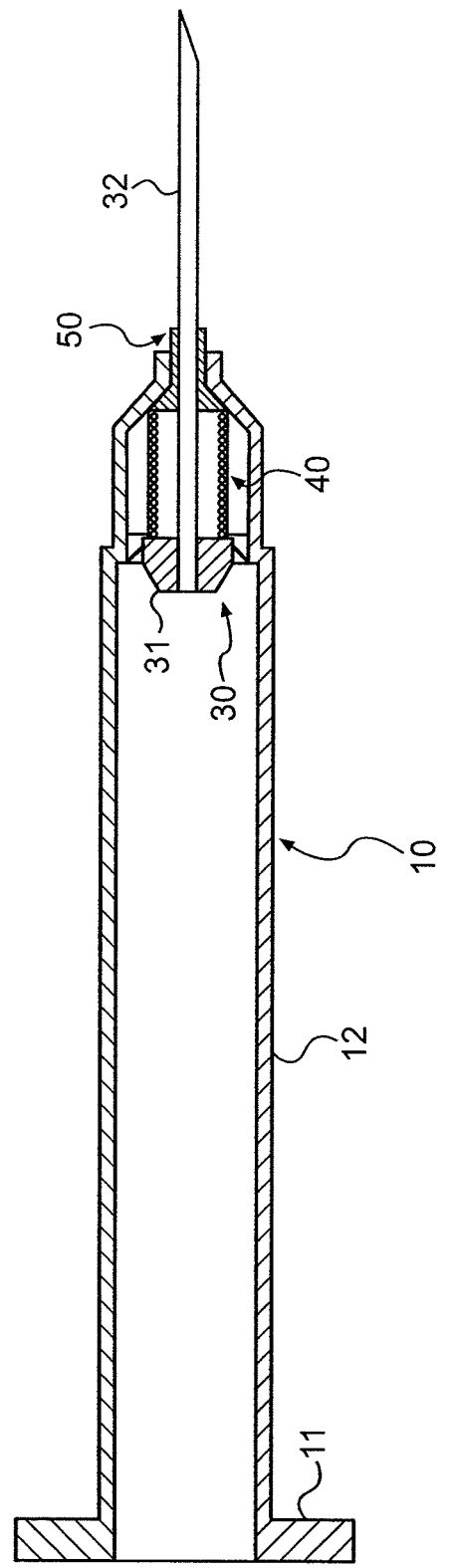
FIG. 15 shows a side cross-section view of the device shown in FIG. 1 with the plunger removed.
Figure 16:
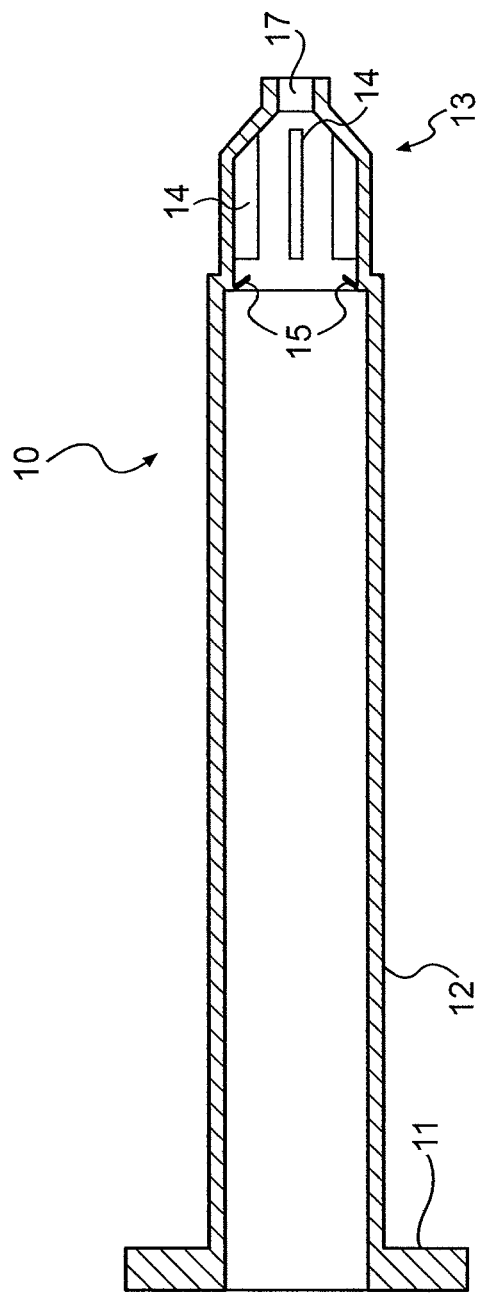
FIG. 16 shows a side cross-section view of the syringe body used in the device shown in FIG. 1.
Figure 19:
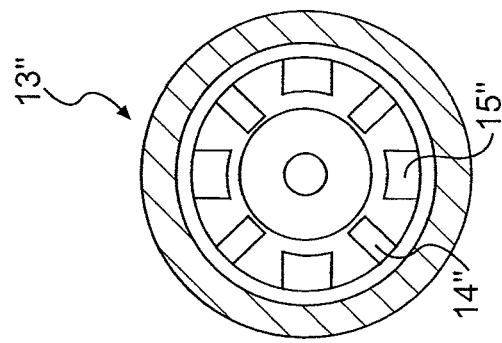
FIG. 19 shows a rear end view of still another embodiment of the syringe body.
Figure 18:
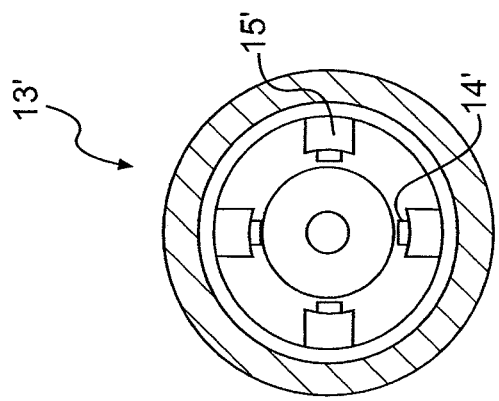
FIG. 18 shows a rear end view of another embodiment of the syringe body.
Figure 17:
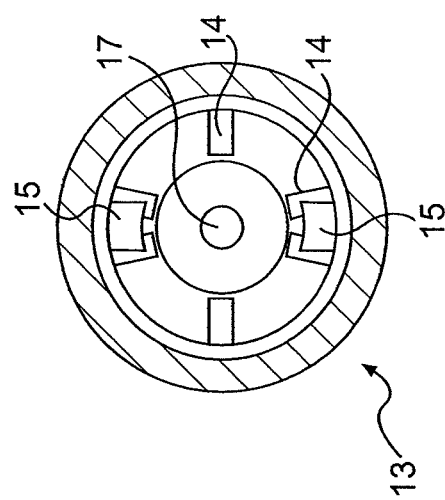
FIG. 17 shows a rear end view of the syringe body shown in FIG. 16.

FIGS. 15-17 show how the syringe body 10 used on the device of FIG. 1 receives therein the seal guide 50, the needle member 30 and the spring 40 before receiving therein the plunger 20 of FIGS. 8 and 9. The body 10, in embodiments, is a one-piece integrally formed member. The body 10 includes a distal flange 11, a main cylindrical section 12, a generally cylindrical proximal end 13, one or more inner radially oriented spaced-apart ribs 14, plural deflectable retaining members 15 which are equally spaced-apart and which are sized and configured to engage with the circumferential recess 33 of the needle unit 30 (see FIG. 20), and a generally cylindrical opening 17 sized and configured to receive therein (in a sealing and/or press-fit manner) the generally cylindrical surface 50a of the sealing guide 50 (see FIG. 26). In embodiments, two oppositely arranged deflectable retaining members 15 are utilized. In embodiments, three equally spaced deflectable retaining members 15 are utilized. In embodiments, between four and eight equally spaced deflectable retaining members 15 are utilized. FIG. 18 shows an optional embodiment wherein section 13' utilizes four equally spaced deflectable retaining members 15' and four ribs 14' which have the same orientation. FIG. 19 shows an optional embodiment wherein section 13" utilizes four equally spaced delectable retaining members 15" and four ribs 14" which are offset with respect to one another. These systems/configurations can be utilized on any of the herein disclosed device embodiments.

FIGS. 20-22 show views of the needle unit 30 used on the device 1 of FIG. 1. The needle unit 30, in embodiments, can be a one-piece integrally formed member. The needle unit 30, in embodiments, utilizes a one-piece needle hub 31 and a one-piece needle 32 that has a distal end secured (e.g., press-fit) within an opening the hub 31. The needle hub 31, in embodiments, also utilizes a tapered section 36 and a circumferential groove or recess 33 which can receive therein the free ends of the deflectable gripping members 15 (see FIG. 6). In embodiments, the needle 32 has a main lumen 34 and a puncturing end 35. In embodiments, the needle 32 can be substantially similar at pistons conventionally used in syringes which include plural external circumferential sealing projections.

FIGS. 23 and 24 show views of the spring 40 used on the embodiment of FIG. 1. FIG. 23 shows the spring 40 in an expanded or relaxed position. In the position shown in FIG. 1, the spring 40 is fully or nearly fully compressed. Expansion of the spring 40 causes the needle unit 30 to retract fully into the plunger 20 (see FIG. 5).

FIGS. 25 and 26 show views of the sealing guide 50 used on the embodiment of FIG. 1. The seal 50 has a generally cylindrical section 50a, a tapered section 50b, and a generally cylindrical opening 50c. The generally cylindrical section 50a is sized and configured to sealingly and frictionally engage with opening 17 in the body 10. The tapered section 50b is sized and configured to sealingly and frictionally engage with a corresponding tapered surface of the body 10. The generally cylindrical opening 50c is sized and configured to sealingly engage with the needle 32. The seal 50, in embodiments, can be a one-piece integrally formed member.

FIG. 27 shows an enlarged partial view of another embodiment of a plunger 20' which can be used on a device of the type shown in FIG. 1. The plunger 20' is similar to that used in FIG. 1 except that the inner seal 25' is axially retained within the plunger 20' via a separately formed ring 29'. The ring 29' is seated in a circumferential recess formed in the seal 25'. In embodiments, a distal circumferential shoulder is sized and configured to break when the plunger 20' is fully depressed. In embodiments, a ring 29' is a frangible ring and is sized and configured to break when the plunger 20' is fully depressed. As with the previous embodiments, the plunger 20' includes a proximal engaging end 24' and a piston 23'. This system/configuration can be utilized on any of the herein disclosed device embodiments.

Figure 28:
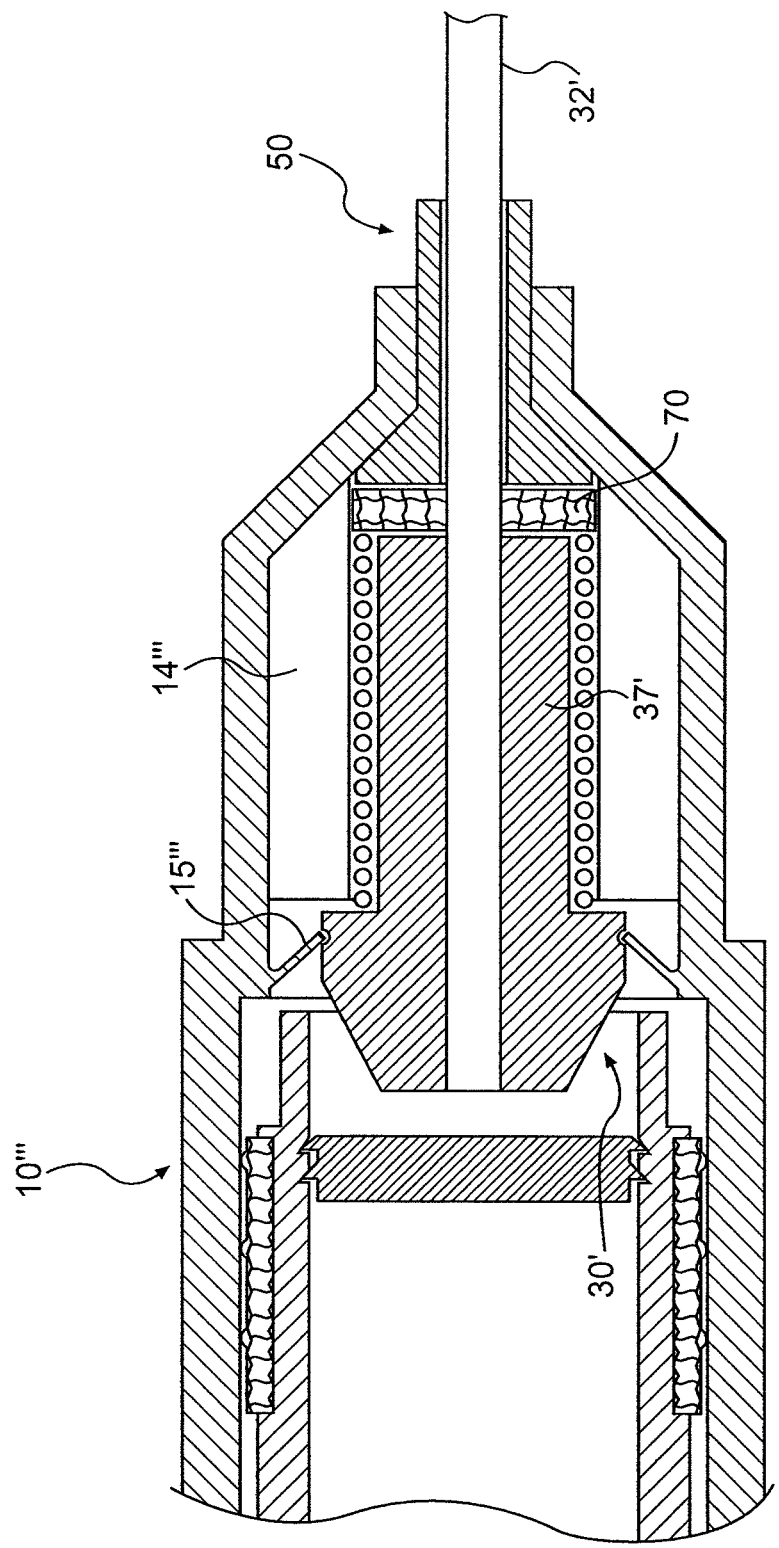
FIG. 28 shows an enlarged partial view of a modified version of the device of FIGS. 1 and 6. In this embodiment, the device of FIGS. 1 and 6 is modified to include a puncturable sealing washer to provided sealing between the needle and the syringe body.

FIG. 28 shows an enlarged partial view of a modified version of the device of FIG. 1. In this embodiment, the device of FIG. 1 is modified to include a puncturable sealing washer 70 to provided sealing between the needle 32' and the guide 50 and/or syringe body 10'''. The needle unit 30' is also modified to include a generally cylindrical section 37'. As with the previous embodiments, the device utilizes ribs 14''' and deflectable retaining members 15'''. This system/configuration can be utilized on any of the herein disclosed device embodiments.

Figure 29:
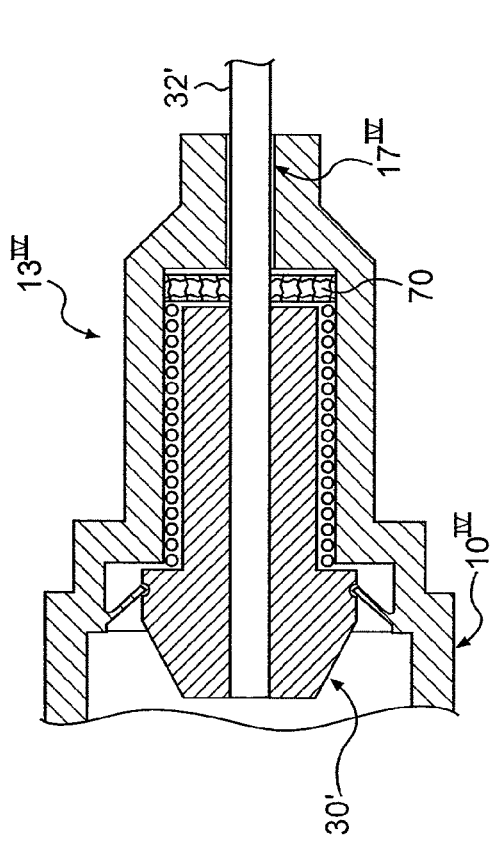
FIG. 29 shows an enlarged partial view of another modified version of the device of FIGS. 1 and 6. In this embodiment, the device of FIGS. 1 and 6 is modified to eliminate the needle sealing guide and to instead include a puncturable sealing washer to provided sealing between the needle and the syringe body.
Figure 30:
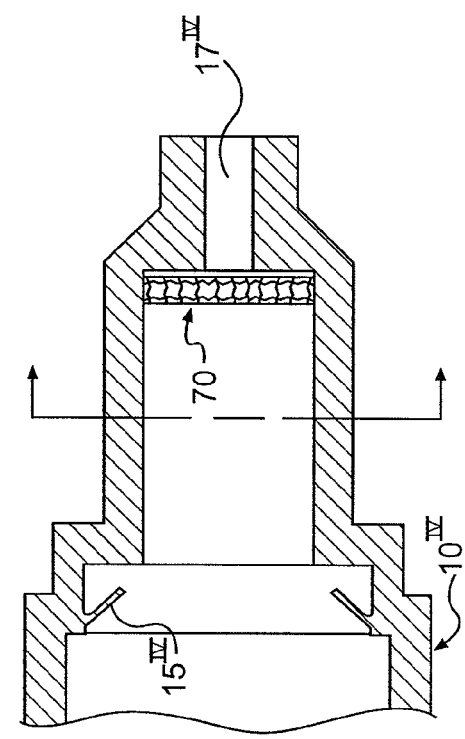
FIG. 30 shows a side cross-section view of the device shown in FIG. 29 with the needle unit and spring removed.
Figure 31:
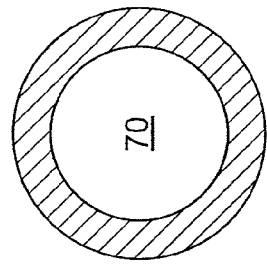
FIG. 31 shows a cross-section view through the section (indicated by arrows) shown in FIG. 30.

FIGS. 29-31 show views of another modified version of the device of FIG. 1. In this embodiment, the device of FIG. 28 is modified to remove the ribs and the guide seal and instead sealing is provided between the opening $17^{IV}$ of the syringe body $10^{IV}$ and the needle 32'. As with the previous embodiments, the device utilizes deflectable retaining members $15^{IV}$. This system/configuration can be utilized on any of the herein disclosed device embodiments.

Figure 32:
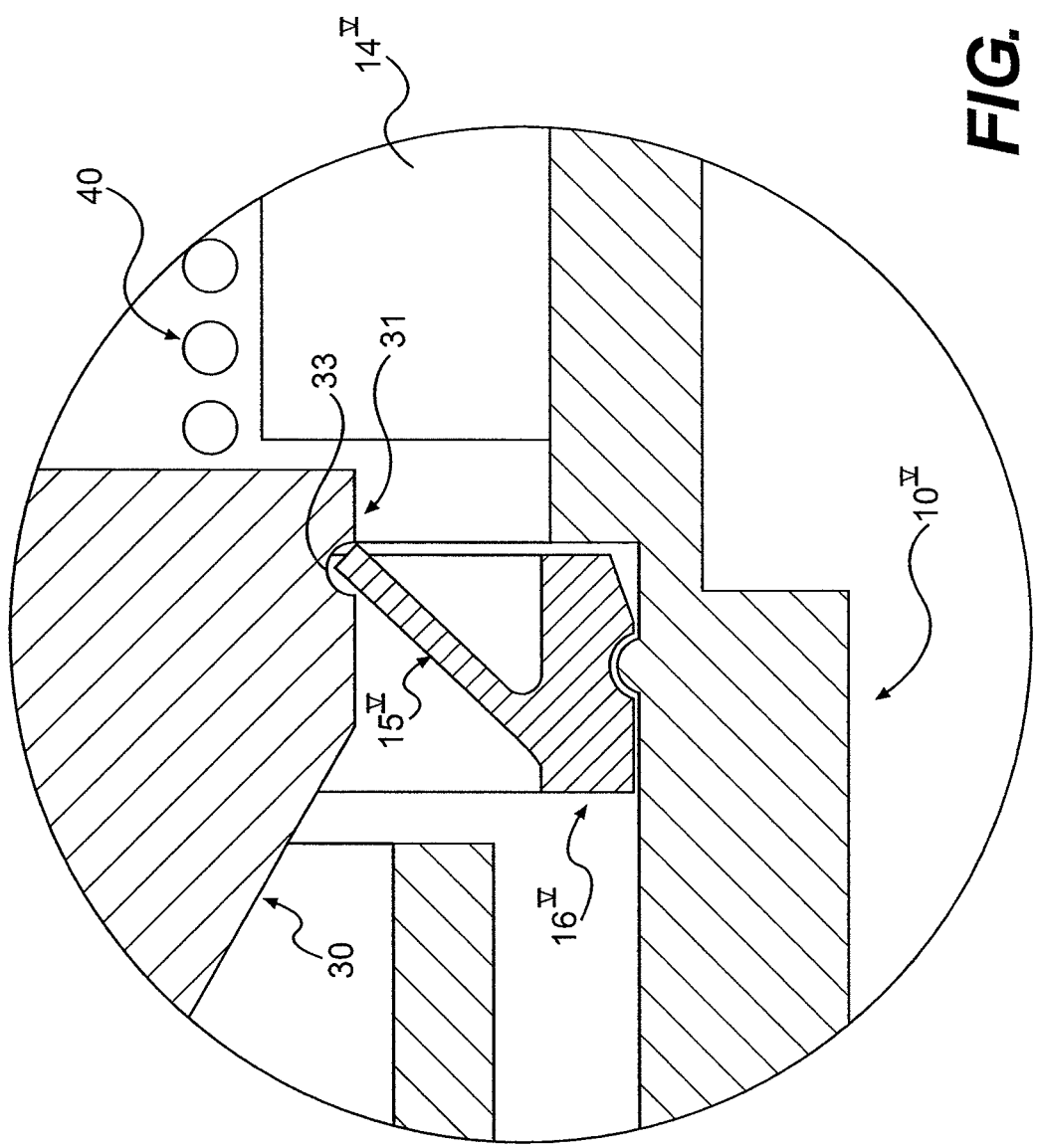
FIG. 32 shows an enlarged partial view of another modified version of the device of FIG. 1. In this embodiment, the device of FIG. 1 is modified to replace the integrally formed deflectable retaining members with a separately formed ring which is axially retained in the syringe body and which has the deflectable retaining members.

FIG. 32 shows an enlarged partial view of another modified version of the device of FIG. 1. In this embodiment, the device of FIG. 1 is modified to replace the integrally formed deflectable retaining members with a separately formed ring $16^V$ which is axially retained in the syringe body $10^V$ via a projection and recess securing arrangement. The ring $16^V$ is a one-piece member that has the deflectable retaining members $15^V$. This system/configuration can be utilized on any of the herein disclosed device embodiments.

FIG. 33 shows an enlarged partial view of another modified version of the device of FIG. 1. In this embodiment, the device of FIG. 1 is modified to include a locking system to prevent re-use of the device as well as an optional vent opening. The locking system has the form of one or more projections LP and one or more recesses LR adapted to receive therein the locking projection LP. The locking system locks the plunger 120 to the syringe body 110 when the plunger 120 is fully or nearly fully depressed. Other configurations can also be utilized such as arranging the locking projections LP on the syringe body 110 and the locking recesses LR on the plunger 120. The projection LP can be, in embodiments, continuous or intermittent and the recess LR can be a circumferential recess. The device can also be modified to utilize an optional vent opening VO in the plunger 120. The locking system prevents re-use of the device. The systems shown in FIG. 33 can be utilized on any of the herein disclosed device embodiments.

Figure 35:
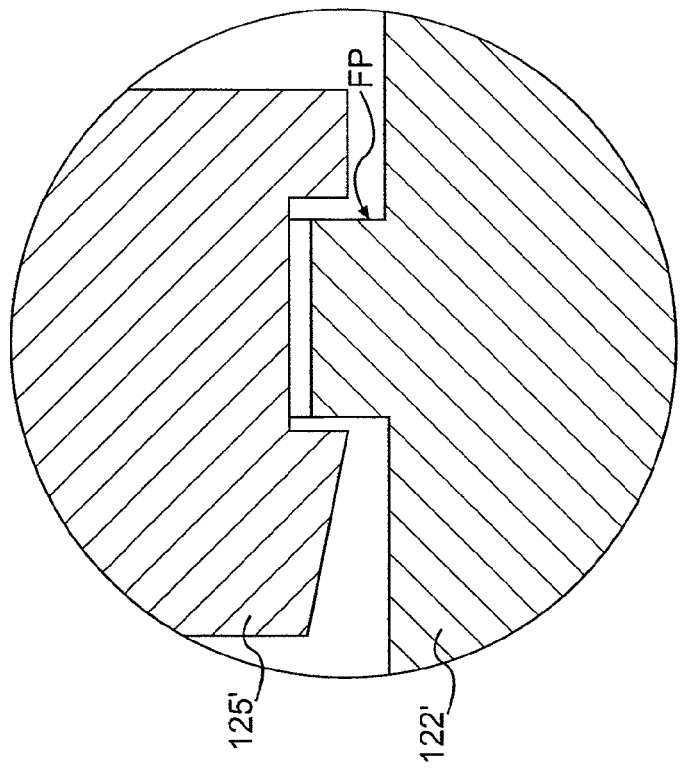
FIGS. 34 and 35 each show an enlarged partial view of another embodiment of a plunger which can be used on a device of the type shown in FIG. 1. The plunger is similar to that used in FIG. 1 except that the inner seal is axially retained within the plunger via a recess and frangible projection system.
Figure 34:
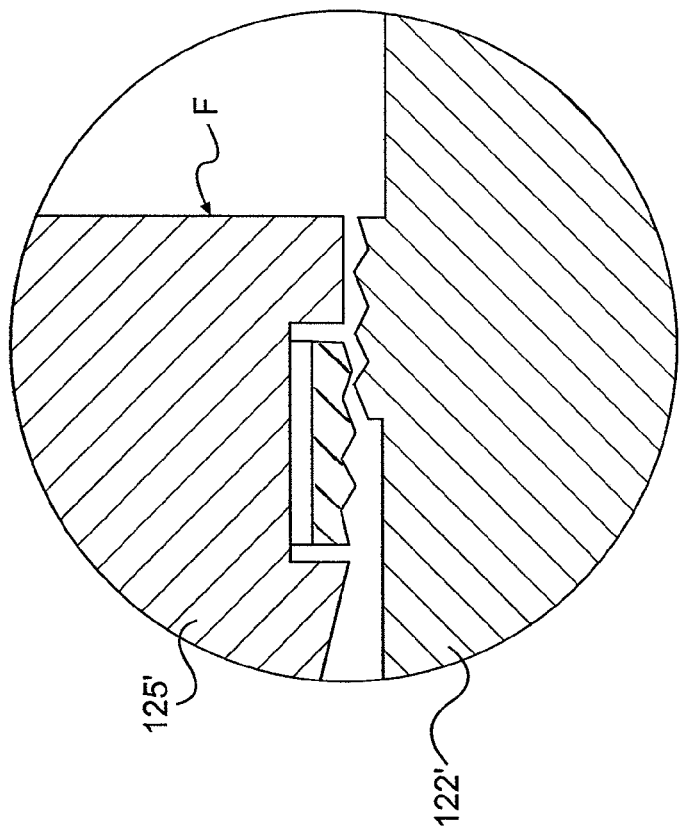

FIGS. 34 and 35 each show an enlarged partial view of another embodiment of a plunger which can be used on a device of the type shown in FIG. 1. The plunger is similar to that used in FIG. 1 except that the inner seal 125' is axially retained within the plunger body 122' via a recess and frangible projection FP. In FIG. 35, the inner seal 125' is axially retained within the plunger. In FIG. 34, the inner seal 125' has been moved back sufficiently under the action of a force F to cause the inner seal 125' to break the frangible projection FP of the plunger. The systems shown in FIGS. 34 and 35 can be utilized on any of the herein disclosed device embodiments.

Figure 36:
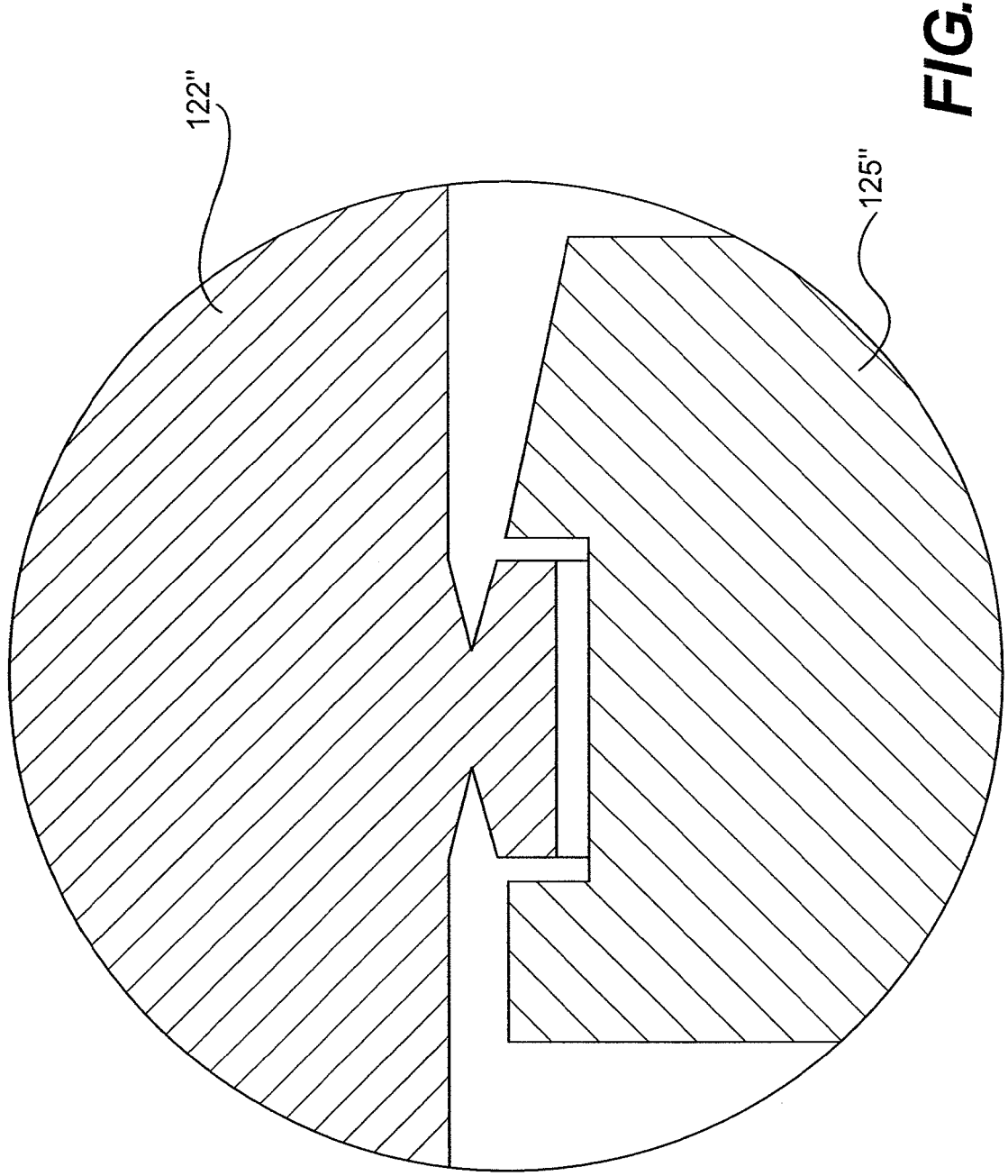
FIG. 36 shows an enlarged partial view of another embodiment of a plunger which can be used on a device of the type shown in FIG. 1. The plunger is similar to that used in FIG. 1 except that the inner seal is axially retained within the plunger via a recess and frangible projection system.

FIG. 36 shows an enlarged partial view of another embodiment of a plunger which can be used on a device of the type shown in FIG. 1. The plunger is similar to that used in FIG. 1 except that the inner seal 125" is axially retained within the plunger body 122" via a recess and a selectively weakened frangible projection FP'. In FIG. 36, the frangible projection FP' of the plunger has annular v-shaped recesses which weaken the projection FP' so that it breaks (via shearing forces) in a predictable manner. The system shown in FIG. 36 can be utilized on any of the herein disclosed device embodiments.

Figure 37:
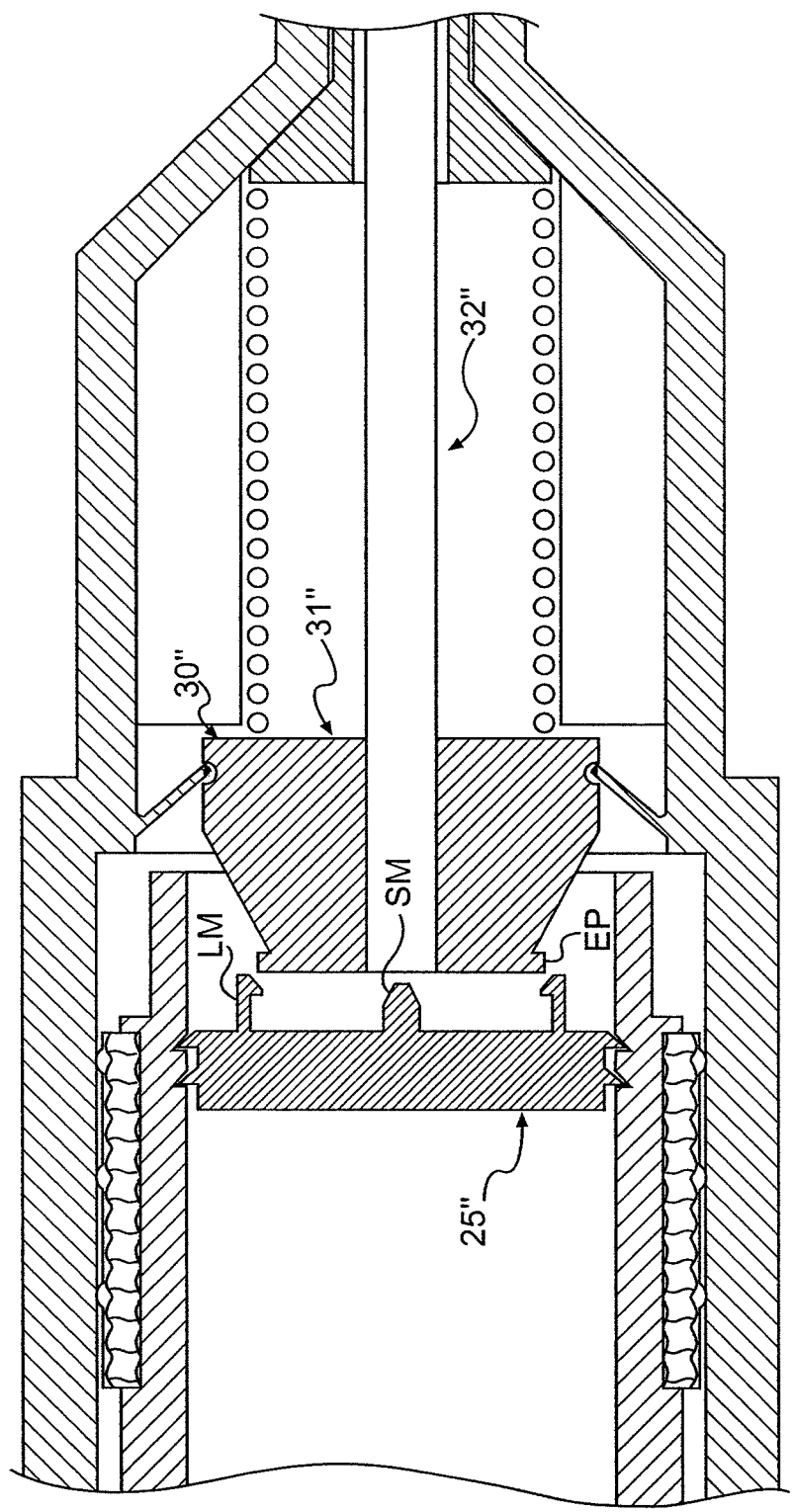
FIG. 37 shows an enlarged partial view of another non-limiting embodiment of a device. The device is similar to that of FIG. 1, except that it utilizes a sealing member that utilizes a sealing member which can extend into the opening of the needle which prevents medication from passing into the needle when it is inserted into the distal end of the needle. The device also utilizes plural locking members which lock to the needle unit when the plunger is moved to the fully depressed position.

FIG. 37 shows an enlarged partial view of another non-limiting embodiment of a device. The device is similar to that of FIG. 1, except that it utilizes a sealing member 25" that utilizes a sealing member SM which can extend into the distal opening of the needle 32" so as to prevent medication from passing into the needle 32" when it is inserted into the distal end of the needle 32". The device also utilizes plural locking members LM which lock to a circumferential engaging projection EP of the needle unit 31" when the plunger is moved to the fully depressed position (indicated by arrow). Once locked to each other, the seal 25" and needle unit 30" retract into the plunger as a unit. The system shown in FIG. 37 can be utilized on any of the herein disclosed device embodiments.

The devices described herein can also utilize one or more features disclosed in prior art documents expressly incorporated by reference in pending U.S. patent application Ser. No. 11/616,196 (Publication No. 2008/0154212). This application and the documents expressly incorporated therein is hereby expressly incorporated by reference in the instant application. Furthermore, one or more of the various parts of the device can preferably be made as one-piece structures by e.g., injection molding, when doing so reduces costs of manufacture. Non-limiting materials for most of the parts include synthetic resins such as those approved for syringes, blood collection devices, or other medical devices. Furthermore, the invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. An injection device comprising:
    a barrel;
    a hollow plunger having a portion structured and arranged to move within the barrel;
    the plunger comprising:
        a proximal end;
        an outer surface arranged axially behind the proximal end; and
        a space disposed in the hollow plunger;
    a needle unit;
    the space being sized and configured to receive therein a distal portion of the needle unit prior to the plunger reaching a substantially fully depressed position;
    at least one releasable retaining member which releasably retains the needle unit in an initial position and that is movable to a position arranged outside the outer surface of the plunger; and
    a safety system that one of:
        automatically causes the needle unit to retract into the plunger when the plunger reaches the substantially fully depressed position; and
        utilizes a frangible or breakable seal arranged within the plunger,
    wherein, during movement of the plunger to the substantially fully depressed position, the space is structured and arranged to receive therein a portion of the distal portion of the needle unit and receives therein the distal portion of the needle unit prior to the needle unit being contacted and prior to the at least one releasable retaining member being contacted, and
    wherein, in the substantially fully depressed position, the at least one releasable retaining member is each of:
        arranged outside the space; and
        in contact with the outer surface, and
    wherein the injection device further comprises each of:
        a locking arrangement that is structured and arranged to lock the needle unit to the frangible or breakable seal; and
        a plugging system spaced from the locking arrangement and that is structured and arranged to plug a distal end of a lumen of the needle unit so as to prevent medication from passing into the lumen.

2. The injection device of claim 1, wherein the injection device is a single-use syringe.

3. The injection device of claim 1, wherein the barrel comprises a cylindrically shaped internal space structured and arranged to receive therein a medicine.

4. The injection device of claim 3, wherein the barrel further comprises a proximal opening within which the needle unit is at least one of:
    press fit; and
    in sealing engagement therewith.

5. The injection device of claim 1, wherein the plunger comprises a piston arranged at a proximal area of the plunger and an actuating end arranged in front of the piston.

6. The injection device of claim 5, wherein the plunger further comprises at least one of:
    the piston being an elastomer or rubber piston;
    a hollow space sized and configured to receive therein the needle unit in its entirety; and
    a locking member adapted to lock with a locking member arranged on the barrel.

7. The injection device of claim 1, wherein the barrel, the plunger, and a hub portion of the needle unit each comprise a synthetic resin material.

8. The injection device of claim 1, wherein the needle unit comprises a generally cylindrical hub and a hollow needle projecting from the hub.

9. The injection device of claim 8, wherein the needle comprises at least one of metal and stainless steel.

* * * * *